United States Patent
Crowley et al.

(10) Patent No.: US 11,779,715 B2
(45) Date of Patent: Oct. 10, 2023

(54) DRY POWDER MEDICAMENT INHALER

(71) Applicant: NORTON (WATERFORD) LIMITED, Waterfod (IE)

(72) Inventors: Peter John Crowley, Waterford (IE); Jan Geert Hazenberg, County Kilkenny (IE); Daniel Buck, County Waterford (IE); Josh Gottesman, Bristol (GB)

(73) Assignee: NORTON (WATERFORD) LIMITED, Waterford (IE)

( * ) Notice: Subject to any disclaimer, the term of this patent is extended or adjusted under 35 U.S.C. 154(b) by 0 days.

(21) Appl. No.: 17/968,555

(22) Filed: Oct. 18, 2022

(65) Prior Publication Data

US 2023/0097991 A1 Mar. 30, 2023

Related U.S. Application Data

(63) Continuation of application No. PCT/EP2022/077065, filed on Sep. 28, 2022.

(30) Foreign Application Priority Data

Sep. 29, 2021 (GB) .................................. 2113921
Jan. 26, 2022 (GB) .................................. 2200986

(51) Int. Cl.
*A61M 15/00* (2006.01)

(52) U.S. Cl.
CPC .... *A61M 15/0051* (2014.02); *A61M 15/0003* (2014.02); *A61M 15/0043* (2014.02); *A61M 2202/064* (2013.01)

(58) Field of Classification Search
CPC ..... A61M 15/00–0003; A61M 15/0013–0016; A61M 15/002–0028;
(Continued)

(56) References Cited

U.S. PATENT DOCUMENTS 5,239,993 A 8/1993 Evans
5,699,789 A 12/1997 Hendricks
(Continued)

FOREIGN PATENT DOCUMENTS

CN 101336118 A 4/2014
EP 1106196 A2 6/2001
(Continued)

*Primary Examiner* — Rachel T Sippel
(74) *Attorney, Agent, or Firm* — Morgan, Lewis & Bockius LLP

(57) ABSTRACT

Disclosed is a dry powder inhaler for delivering medicament from at least one blister pack, each blister pack having a plurality of spaced-apart blister pockets containing doses of the medicament. The inhaler comprises: a housing for accommodating unused and used portions of the at least one blister pack together with a dispensing mechanism for simultaneously opening at least two blister pockets at a time; and a manifold component through which air can be drawn in use of the inhaler. The manifold component comprises: first and second air inlet openings for receiving external air a first air outlet opening for providing the external air to a first opened blister pocket and a first medicament inlet opening for receiving air-entrained medicament from the first opened blister pocket, the first air outlet opening and the first medicament inlet opening being arranged side-by-side to enable simultaneous communication with the first opened blister pocket; a second air outlet opening for providing the external air to a second opened blister pocket and a second medicament inlet opening for receiving air-entrained medicament from the second opened blister pocket, the second air outlet opening and the second medicament inlet opening being arranged side-by-side to enable simultaneous communication with the second opened blister pocket; and a medicament outlet opening for delivery of the air-entrained medicament from the first and second opened blister pockets to the user, the first and second medicament inlet openings (Continued)

being fluidly connected to the medicament outlet opening by a medicament delivery conduit formed in the manifold component. The first and second air inlet openings are fluidly connected to the first and second air outlet openings by respective first and second air conduits in the manifold component, wherein the air conduits are separately provided so that the external air from each of the first and second air inlet openings does not mix with the external air from the other of the first and second air inlet openings before reaching the first and second opened blister pockets.

29 Claims, 12 Drawing Sheets

(58) Field of Classification Search
CPC . A61M 15/0043–0046; A61M 15/0051–0055; A61M 15/0058–0065; A61M 15/0068–008; A61M 2202/064
See application file for complete search history.

(56) References Cited

U.S. PATENT DOCUMENTS

| | | | |
|---|---|---|---|
| 2002/0066451 | A1 | 6/2002 | Davies et al. |
| 2003/0075172 | A1 | 4/2003 | Johnson et al. |
| 2006/0196504 | A1* | 9/2006 | Augustyn ......... A61M 15/0043 128/203.15 |
| 2009/0314291 | A1* | 12/2009 | Anderson ........... A61M 15/007 128/203.15 |
| 2021/0386945 | A1* | 12/2021 | Ahern .................... A61M 11/00 |
| 2021/0402106 | A1* | 12/2021 | Trexler ................. A61M 11/02 |

FOREIGN PATENT DOCUMENTS

| | | |
|---|---|---|
| EP | 0634184 B1 | 10/2001 |
| EP | 1844806 A1 | 10/2007 |
| EP | 2082760 A1 | 7/2009 |
| EP | 2082764 A1 | 7/2009 |
| EP | 2082769 B1 | 7/2009 |
| EP | 2198907 A1 | 6/2010 |
| EP | 3856303 A1 | 8/2021 |
| GB | 2242134 A | 9/1991 |
| GB | 2407042 A | 4/2005 |
| JP | H09248342 A | 9/1997 |
| JP | 2000217920 A | 8/2000 |
| JP | 2001070403 A | 3/2001 |
| JP | 2014140755 A | 8/2014 |
| WO | 03/061744 A1 | 7/2003 |
| WO | 2006/066909 A1 | 6/2006 |
| WO | 2006/066910 A1 | 6/2006 |
| WO | 2007/012871 A1 | 2/2007 |
| WO | 2007/068896 A1 | 6/2007 |
| WO | 2007/068900 A2 | 6/2007 |
| WO | 2007/129127 A1 | 11/2007 |
| WO | 2009/092520 A1 | 7/2009 |
| WO | 2010/040779 A2 | 4/2010 |
| WO | 2010/133321 A1 | 11/2010 |
| WO | 2010/133323 A1 | 11/2010 |
| WO | 2010/135253 A2 | 11/2010 |
| WO | 2010/135340 A2 | 11/2010 |
| WO | 2010/136134 A1 | 12/2010 |
| WO | 2011/129785 A1 | 10/2011 |
| WO | 2011/129790 A1 | 10/2011 |
| WO | 2015/006838 A1 | 1/2015 |
| WO | 2018/094392 A1 | 5/2018 |
| WO | 2020/025977 A1 | 2/2020 |
| WO | 2020/053878 A1 | 3/2020 |
| WO | 2021/099328 A1 | 5/2021 |

* cited by examiner

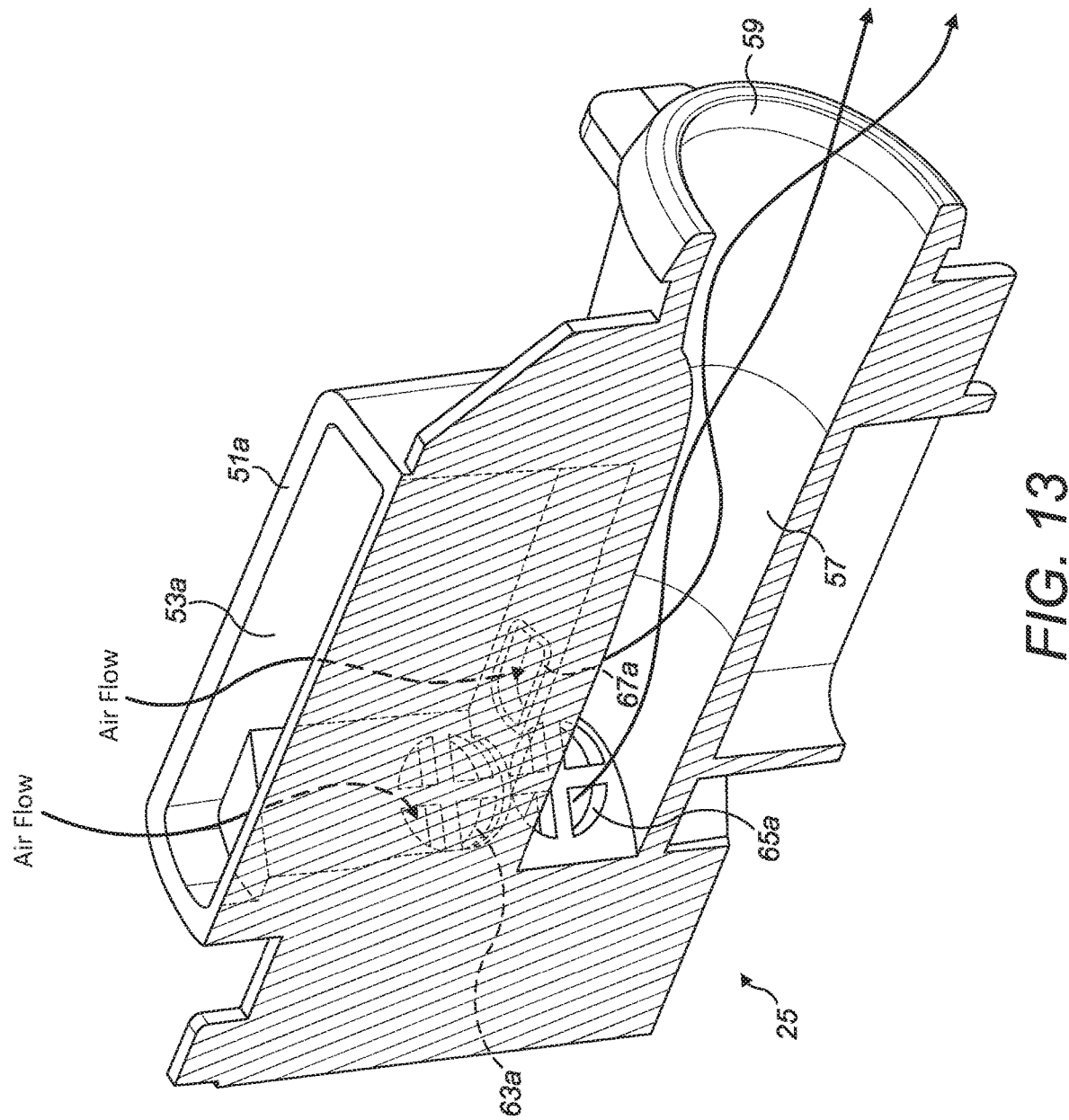

DRY POWDER MEDICAMENT INHALER

CROSS REFERENCE TO RELATED APPLICATIONS

This application is a Continuation of International Patent Application No. PCT/EP2022/077065 filed Sep. 28, 2022, which claims priority to GB Patent Application No. 2200986.4 filed Jan. 26, 2022 and GB Patent Application No. 2113921.7 filed Sep. 29, 2021, each of which is hereby incorporated by reference in its entirety.

FIELD OF THE INVENTION

This invention relates to a dry powder inhaler. In particular, this invention relates to a dry powder inhaler for delivering medicament from at least one elongate blister pack, wherein the blister pack has a plurality of spaced-apart blister pockets containing doses of the medicament.

BACKGROUND OF THE INVENTION

Inhalers for drug delivery to a user by inhalation are well-known. Such devices include metered-dose inhalers and dry powder inhalers.

Metered dose inhalers typically comprise a container containing a propellant and a liquid solution or suspension of a medicament. Metered dose inhalers further include a dispensing valve which, when actuated, causes the medicament to be forced out of the container by expansion of the propellant in the form of an aerosol.

Dry powder inhalers, on the other hand, typically comprise a supply of the medicament in dry powder form, and are arranged to permit the user to inhale discrete doses from the supply of powder medicament.

Some dry powder inhalers comprise a bulk reservoir of powder medicament, with a dispensing mechanism being configured to separate a dose of the medicament from the reservoir and make it available for inhalation by the user. Other types of dry powder inhaler comprise a plurality of pre-metered doses of powder medicament in containers, for example in capsules or blisters, and a dispensing mechanism which is configured to open the containers and make the doses of medicament available for inhalation by the user.

One such type of dry powder inhaler comprises a medicament carrier in the form of a blister pack having a plurality of spaced-apart blister pockets containing doses of the medicament. The inhaler comprises a manually-operated dispensing mechanism for moving a medicament dose of the medicament carrier to a dispensing position in the inhaler, and for placing the medicament dose in fluid communication with an air flow path of the inhaler, for example by piercing or peeling open the blisters, ready for inhalation by the user.

An inhaler of this type is described in GB 2242134 A. The dispensing mechanism of this device is operated by a lever, which causes a blister to be moved to the dispensing position of the inhaler and peeled open. Another inhaler of this type is described in WO 2007/068896 A1. The dispensing mechanism of this inhaler is operated by a rotatable mouthpiece cover, the opening of which causes a blister to be moved to the dispensing position of the inhaler and peeled open.

It is noted that dry powder inhalers of this type can be used for combination therapy, whereby a plurality of different powder medicaments can be dispensed for simultaneous inhalation by the user. The different medicaments can be provided in groups of blisters of the blister pack, which can then be opened together (in groups). Alternatively, the different medicaments can be provided in different blister packs, with the dispensing mechanism simultaneously acting on all of the blister packs to open a blister of each pack together. Such use is advantageous where the different medicaments cannot be stored together, for example because of chemical incompatibilities.

Dry powder inhalers of the type described above may comprise a manifold component which defines a part of an air flow path through the inhaler. In particular, the manifold is arranged to direct air (through an air conduit) from an air inlet of the inhaler to the opened blisters, and to direct air-entrained medicament (through a medicament delivery conduit) from the opened blisters to a mouthpiece of the inhaler. Inhalation-induced air flow through the manifold causes the medicament in the opened blisters to be entrained by the air, which flows through the opened blisters, and across the medicament, so that the air-entrained medicament can be inhaled by the user. By way of example, WO 2007/068896 A1 discloses a manifold of this type in which an air bypass hole is provided so that a bleed air flow disruptively impacts the flow of air-entrained medicament.

The present inventors have recognised a problem that arises in relation to dry powder inhalers of the type described above, in particular such inhalers for use in combination therapy whereby a plurality of different powder medicaments can be dispensed simultaneously. In particular, when different medicaments are simultaneously delivered from different opened blisters, it has been found that optimisation of the delivery of the individual medicaments can be difficult to achieve.

SUMMARY OF THE INVENTION

The invention provides a dry powder inhaler for delivering medicament from at least one blister pack, each blister pack having a plurality of spaced-apart blister pockets containing doses of the medicament, the inhaler comprising:

a housing for accommodating unused and used portions of the at least one blister pack together with a dispensing mechanism for simultaneously opening at least two blister pockets at a time; and a manifold component through which air can be drawn in use of the inhaler, wherein the manifold component comprises:

first and second air inlet openings for receiving external air;

a first air outlet opening for providing the external air to a first opened blister pocket and a first medicament inlet opening for receiving air-entrained medicament from the first opened blister pocket, the first air outlet opening and the first medicament inlet opening being arranged side-by-side to enable simultaneous communication with the first opened blister pocket;

a second air outlet opening for providing the external air to a second opened blister pocket and a second medicament inlet opening for receiving air-entrained medicament from the second opened blister pocket, the second air outlet opening and the second medicament inlet opening being arranged side-by-side to enable simultaneous communication with the second opened blister pocket; and a medicament outlet opening for delivery of the air-entrained medicament from the first and second opened blister pockets to the user, the first and second medicament inlet openings being fluidly connected to the medicament outlet opening by a medicament delivery conduit formed in the manifold component.

According to the invention, the first and second air inlet openings are fluidly connected to the first and second air outlet openings by respective first and second air conduits, wherein the air conduits are separately provided in the manifold component so that the external air from each of the first and second air inlet openings does not mix with the external air from the other of the first and second air inlet openings before reaching the first and second opened blister pockets.

By providing separate first and second air conduits connecting the air inlet openings and the air outlet openings of the manifold component, the invention provides at least partly independent air flow paths for the air that passes through the first and second opened blister pockets, in particular the part of the air flow paths that are upstream of the opened blister pockets. This allows the air flow paths to be adapted, or "tuned", to suit the different blister pockets, for example different medicament formulations having different aerodynamic or flow properties, or different dose sizes contained in the blister pockets.

The inventive approach of adapting the design of the inhaler, in particular the manifold design, to the physical properties of the medicament formulations may to at least some extent replace the conventional approach of adapting the physical properties of a medicament formulation, for example its particle size distribution, to the inhaler design. This inventive approach is, however, only made possible by the inventive provision of the separate air conduits for the respective opened blister pockets. It is to be noted that advantageous effects may also arise in relation to embodiments that are used with identical blister pockets and medicaments, in which case the air flow paths may be adapted so that the same medicament in the first and second opened blister pockets may be entrained in different ways and/or at slightly different times.

Furthermore, it has been found that the separate air conduits of the invention serve to reduce the risk of unintentional mixing of the medicaments from the blister pockets prior to inhalation by the user, for example in the event that the user accidentally exhales slightly before inhaling (which exhalation might otherwise lead to mixing of the medicaments in a combined air conduit upstream of the blisters).

In embodiments, the dry powder inhaler further comprises a mouthpiece component through which a user is able to inhale the air-entrained medicament from the first and second opened blister pockets, wherein the mouthpiece defines an opening which is fluidly connected to the medicament outlet opening of the manifold component. In use, the air-entrained medicament passes straight from the medicament outlet opening of the manifold component to the mouthpiece.

The air flow paths for the first and second opened blisters may be adapted, or tuned, in a variety of different ways. For example, the first and second air conduits may have different air flow resistances. A larger air flow resistance may, for example, be appropriate for a powder medicament having aerodynamic properties that make it easier to entrain in the air flow, for example a powder medicament that has a lower bulk density, or a powder medicament in which the particles have less of a tendency to "stick" together. Such powder medicaments are able to be adequately entrained in the reduced air flow that results from the higher air flow resistance.

Conversely, a smaller air flow resistance may, for example, be appropriate for a powder medicament having aerodynamic properties that make it more difficult to entrain in the air flow, for example a powder medicament that has a higher bulk density, or a powder medicament in which the particles have more of a tendency to "stick" together.

The different air flow resistances of the first and second air conduits may be provided in a variety of different ways. For example, different flow resistances may be provided by configuring the first and second air conduits to have different lengths and/or different cross sections and/or different cross sectional areas. Additionally or alternatively, the different air flow resistances may be provided by arranging air flow restriction elements, such as baffles or other obstacles, inside one or both of the first and second air conduits.

In embodiments, the manifold component may further comprise: a first air bypass passage providing direct fluid communication between the first air conduit and the medicament delivery conduit; and a second air bypass passage providing direct fluid communication between the second air conduit and the medicament delivery conduit. The provision of separate and independent air bypass passages between the first and second air conduits and the medicament delivery conduit provides further scope for the air flow paths associated with the different opened blister pockets to be adapted, or tuned. For example, the air bypass passages may be adapted to vary the proportions of the air flow into the first and second air inlet openings (which air flow passes through the respective opened blisters).

For example, the first and second air bypass passages may have different lengths and/or different cross sections and/or different cross sectional areas. Additionally or alternatively, air flow restriction elements may be arranged inside the first and second air bypass passages. Additionally or alternatively, the first and second air bypass passages may be provided at different positions along the medicament delivery conduit, which allows for the bleed air flow through the bypass passages to disruptively impact the air flow in the medicament delivery conduit at multiple positions along its length, to thereby further improve turbulence and deagglomeration of the powder medicament.

In general, the first and second air conduits may be arranged in the manifold component to be adjacent to the medicament delivery conduit and separated therefrom by thin walls, wherein the first and second air bypass passages are formed as apertures in the walls.

The manifold component may be provided as a moulded plastics component, optional a unitary moulded plastics component. In this way, a manifold component having relatively complicated structures can be provided in a cost effective manner.

The moulded plastics component may be formed of a material selected from the group consisting of: polyolefins, including polyethylene, in particular high density polyethylene (HDPE), and polypropylene; polyesters, including polyethylene terephthalate; polyamides, including nylons; thermosetting polymers, including urea-formaldehyde, melamine, epoxy resins and polyimides; and mixtures or copolymers thereof.

In embodiments, the first and second air conduits may be configured to collimate the external air (i.e. induce parallel flow through the conduits). The first and second air outlet openings may each define a central axis which is substantially normal to the plane of the blister pack. In this way the air may be caused to flow directly towards the opened blisters for the purpose of entraining the medicament. Side walls of the first and second air conduits may be formed entirely by the manifold component (i.e. and not by the blister strip itself).

In embodiments, the first and second air inlet openings may define the only points of entry for external air into the manifold component, and optionally they may define the only points of entry for external air into the entire inhaler.

The first and second air conduits may be arranged to be side-by-side and parallel to each other, and separated by a wall. The first and second air conduits may each have an elongate cross section, with the long sides of the cross sections facing each other.

The medicament delivery conduit may have a circular, oval or elliptical cross section, and the medicament delivery conduit may tapers along its length with an increasing cross sectional area in the direction of air flow.

The first and second air conduits may extend in a direction substantially perpendicular to the direction in which the medicament delivery conduit extends.

In embodiments, the dry powder inhaler is arranged so that, in use, air is directed from the first and second air outlet openings of the manifold component into the respective first and second opened blisters, and air-entrained medicament is directed from the first and second opened blisters into the respective first and second medicament inlet openings.

Some embodiments may provide for simultaneous delivery of powdered medicament from three or more opened blister pockets, which blister pockets may be formed in the same and/or different blister strips. In this case, the dispensing mechanism is configured for simultaneously opening at least three blister pockets at a time, and the manifold component further comprises:

a third air inlet opening for receiving external air, and a third air outlet opening for providing the external air to a third opened blister pocket and a third medicament inlet opening for receiving air-entrained medicament from the third opened blister pocket, the third air outlet opening and the third medicament inlet opening being arranged side-by-side to enable simultaneous communication with the third opened blister pocket, wherein the medicament outlet opening of the manifold component is configured for delivery of the air-entrained medicament from the third opened blister pocket to the user, the third medicament inlet opening being fluidly connected to the medicament outlet opening of the manifold component by the medicament delivery conduit, and wherein the third air inlet opening is fluidly connected to the third air outlet opening by a third air conduit, wherein the third air conduit is provided separately from the first and second air conduits so that the external air from either of the first and second air inlet openings does not mix with the external air from the third air inlet opening before reaching the third opened blister pocket.

Other embodiments may provide for simultaneous delivery of powdered medicament from more than three opened blister pockets, in which case the the manifold component would be provided with further features for each additional blister.

The dry powder inhaler may further comprise the dispensing mechanism for simultaneously opening at least two blister pockets at a time (the inhaler could in principle be provided without the dispensing mechanism, with the dispensing mechanism then forming part of a medicament cartridge, for example).

The dispensing mechanism may comprise a peeling mechanism which is arranged to open the blister pockets by gradually peeling a cover layer of the at least one blister pack from a base layer of the at least one blister pack.

The dispensing mechanism may also comprise an indexing mechanism which is arranged to move the at least one blister pack so that the first opened blister pocket is aligned with the first air outlet opening and the first medicament inlet opening, and the second opened blister pocket is aligned with the second air outlet opening and the second medicament inlet opening. In this way, medicament from the first and second opened blister pockets can be delivered simultaneously.

Embodiments of the invention may further comprise the at least one blister pack, wherein each blister pack comprises an elongate base layer defining spaced-apart blister openings containing medicament doses, and a cover layer adhesively bonded to the base layer to close the blister openings, and wherein the cover layer is arranged to be peeled from the base layer.

The dry powder inhaler may comprise a single blister pack, and the dispensing mechanism is then arranged to open at least two blister pockets of the blister pack at a time, these being the first and second opened blister pockets, and to move the blister pack so that the first opened blister pocket is aligned with the first air outlet opening and the first medicament inlet opening, and the second opened blister pocket is aligned with the second air outlet opening and the second medicament inlet opening. In this way, the dry powder inhaler can be used for simultaneous inhalation of different medicaments from the first and second opened blister pockets.

The first and second blister pockets may have the same or a different shape and/or volume.

The first and second blister pockets may contain essentially any inhalable powder medicament, for example medicaments for the treatment of respiratory disorders such as asthma, chronic obstructive pulmonary disease (COPD), bronchitis and chest infections. Suitable powder medicaments may include for example any one of long acting beta antagonists (LABA), short acting beta antagonists (SABA), corticosteroids (ICS), long acting muscarinic antagonists (LAMA), short acting muscarinic antagonists (SAMA), or any other drug that can be administered via inhalation including combination thereof. Examples for such drugs include but are not limited to budesonide, formoterol, beclomethasone, fluticasone, salmeterol, albuterol, salbutamol, indacaterol, tiotropium, ipratropium, glycorpyrronium, umeclidinium, vilanterol and combination thereof. Where fluticasone is mentioned, this term is intended to cover any suitable ester form, in particular fluticasone propionate or fluticasone furoate. The powder medicaments may be suitable for combination therapy.

For example, the different medicaments for simultaneous inhalation may comprise:

LABA or SABA in the first blister pocket and an ICS in the second blister pocket; or LABA or SABA in the first blister pocket and LAMA or SAMA in the second blister pocket; or LABA or SABA and LAMA or SAMA in the first blister pocket and ICS in the second blister pocket, or budesonide in the first blister pocket and formoterol in the second blister pocket; or beclomethasone in the first blister pocket and formoterol in the second blister pocket; or fluticasone in the first blister pocket and salmeterol in the second blister pocket, or fluticasone in the first blister pocket and albuterol in the second blister pocket, or fluticasone in the first blister pocket and vilanterol in the second blister pocket, or umeclidinium in the first blister pocket and vilanterol in the second blister pocket, or two selected from umeclidinium, fluticasone and vilanterol in the first blister pocket, the remaining medicament from umeclidinium, fluticasone and vilanterol in the second blister pocket.

The first and second blister pockets of the blister pack may contain a different mass or volume of the respective medicaments, and/or contain respective medicaments having different particle size distributions.

Alternatively, the dry powder inhaler may comprise first and second blister packs (for example exactly two blister packs), and the dispensing mechanism is then arranged to simultaneously open a blister pocket of each of the first and second blister packs, these being the first and second opened blister pockets, and to simultaneously move the first and second blister packs so that the first opened blister pocket is aligned with the first air outlet opening and the first medicament inlet opening, and the second opened blister pocket is aligned with the second air outlet opening and the second medicament inlet opening. In this way, the dry powder inhaler can be used for simultaneous inhalation of different medicaments from the first and second opened blister pockets.

The blister pockets of the first and second blister packs have a different shape and/or volume.

The first and second blister packs may contain essentially any inhalable powder medicament, for example medicaments for the treatment of respiratory disorders such as asthma, chronic obstructive pulmonary disease (COPD), bronchitis and chest infections. Suitable powder medicaments may include for example any one of long acting beta antagonists (LABA), short acting beta antagonists (SABA), corticosteroids (ICS), long acting muscarinic antagonists (LAMA), short acting muscarinic antagonists (SAMA), or any other drug that can be administered via inhalation including combination thereof. Examples for such drugs include but are not limited to budesonide, formoterol, beclomethasone, fluticasone, salmeterol, albuterol, salbutamol, indacaterol, tiotropium, ipratropium, glycorpyrronium, umeclidinium, vilanterol and combination thereof. Where fluticasone is mentioned, this term is intended to cover any suitable ester form, in particular fluticasone propionate or fluticasone furoate. The powder medicaments may be suitable for combination therapy.

For example, the different medicaments for simultaneous inhalation may comprise:

LABA or SABA in the first blister pack and an ICS in the second blister pack; or LABA or SABA in the first blister pack and LAMA or SAMA in the second blister pack; or LABA or SABA and LAMA or SAMA in the first blister pack and ICS in the second blister pack, or budesonide in the first blister pack and formoterol in the second blister pack; or beclomethasone in the first blister pack and formoterol in the second blister pack; or fluticasone in the first blister pack and salmeterol in the second blister pack, or fluticasone in the first blister pack and albuterol in the second blister pack, or fluticasone in the first blister pack and vilanterol in the second blister pack, or umeclidinium in the first blister pack and vilanterol in the second blister pack, or two selected from umeclidinium, fluticasone and vilanterol in the first blister pack, the remaining medicament from umeclidinium, fluticasone and vilanterol in the second blister pack.

The pockets of the first and second blister packs may contain a different mass or volume of the respective medicaments, and/or contain respective medicaments having different particle size distributions.

BRIEF DESCRIPTION OF THE DRAWINGS

Embodiments of the invention will now be described in more detail and by way of non-limiting examples with reference to the accompanying drawings, in which:

FIG. 13 is a view corresponding to FIG. 11 showing air flow through the manifold component.

DETAILED DESCRIPTION OF THE EMBODIMENTS

Figure 1:
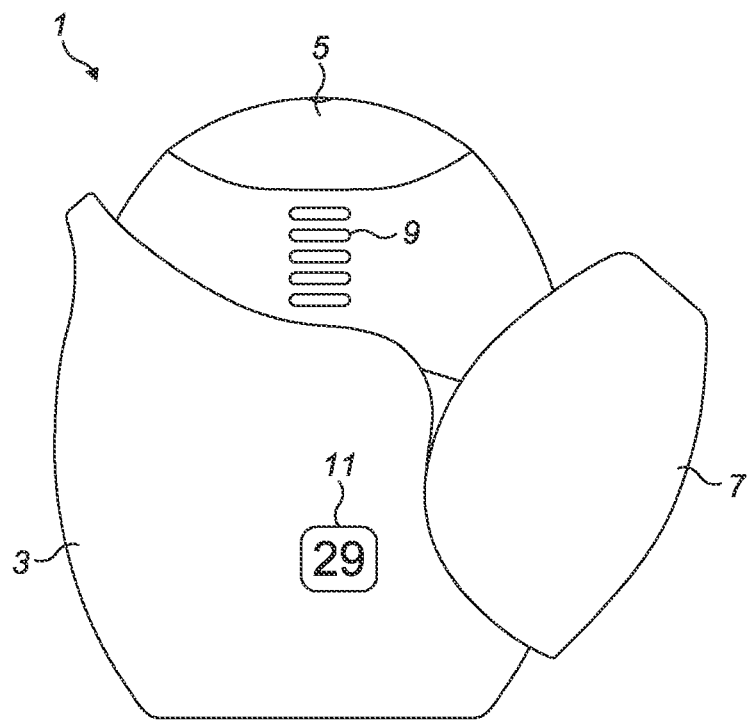
FIG. 1 is a perspective view of a dry powder inhaler according to an embodiment of the invention.

It should be understood that the detailed description, while indicating exemplary embodiments of the inventive dry powder inhaler, are intended for the purposes of illustration only and are not intended to limit the scope of the invention. Features, aspects, and advantages of the inhaler will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a dry powder inhaler for delivering medicament from at least one blister pack, each blister pack having a plurality of spaced-apart blister pockets containing doses of the medicament. The inhaler comprises a housing for accommodating unused and used portions of the at least one blister pack together with a dispensing mechanism for simultaneously opening at least two blister pockets at a time; the inhaler also comprises a manifold component through which air can be drawn in use of the inhaler.

The manifold component comprises:

first and second air inlet openings for receiving external air;

a first air outlet opening for providing the external air to a first opened blister pocket and a first medicament inlet opening for receiving air-entrained medicament from the first opened blister pocket, the first air outlet opening and the first medicament inlet opening being arranged side-by-side to enable simultaneous communication with the first opened blister pocket;

a second air outlet opening for providing the external air to a second opened blister pocket and a second medicament inlet opening for receiving air-entrained medicament from the second opened blister pocket, the second air outlet opening and the second medicament inlet opening being arranged side-by-side to enable simultaneous communication with the second opened blister pocket; and a medicament outlet opening for delivery of the air-entrained medicament from the first and second opened blister pockets to the user, the first and second medicament inlet openings being fluidly connected to the medicament outlet opening by a medicament delivery conduit formed in the manifold component.

According to the invention, the first and second air inlet openings are fluidly connected to the first and second air outlet openings by respective first and second air conduits, wherein the air conduits are separately provided in the manifold component so that the external air from each of the first and second air inlets does not mix with the external air from the other of the first and second air inlets before reaching the first and second opened blister pockets.

By providing separate first and second air conduits connecting the air inlet openings and the air outlet openings of the manifold component, the invention provides at least partly independent air flow paths for the air that passes through the first and second opened blister pockets, in particular the part of the air flow paths that are upstream of the opened blister pocket. This allows the air flow paths to be adapted, or "tuned", to suit the different blister pockets, for example different medicament formulations or different dose sizes contained in the blister pockets.

Figure 2:
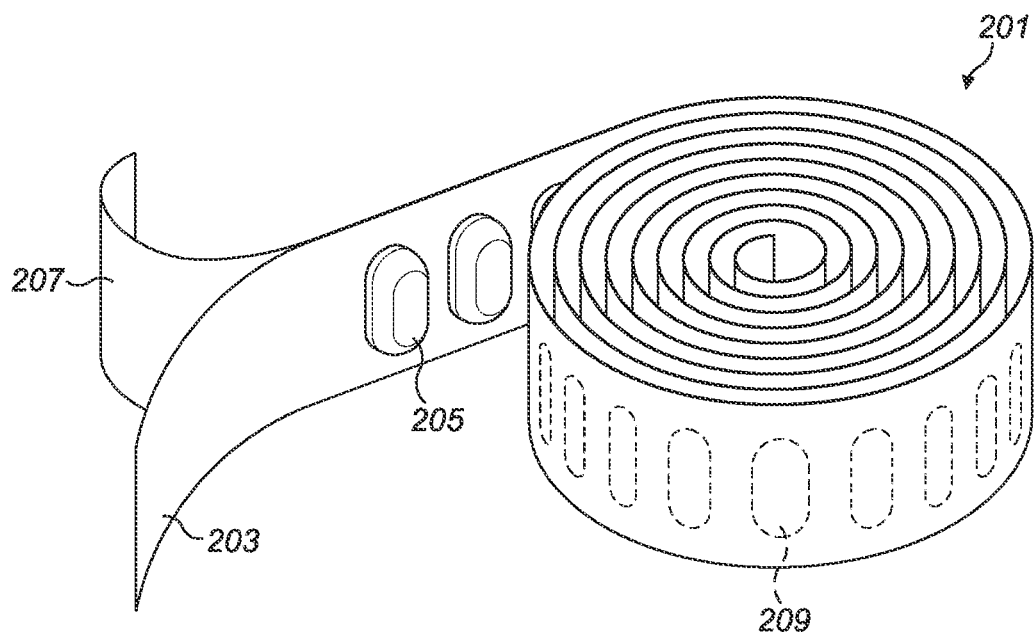
FIG. 2 is a perspective view of a medicament carrier for use in the dry powder inhaler shown in FIG. 1.
Figure 3:
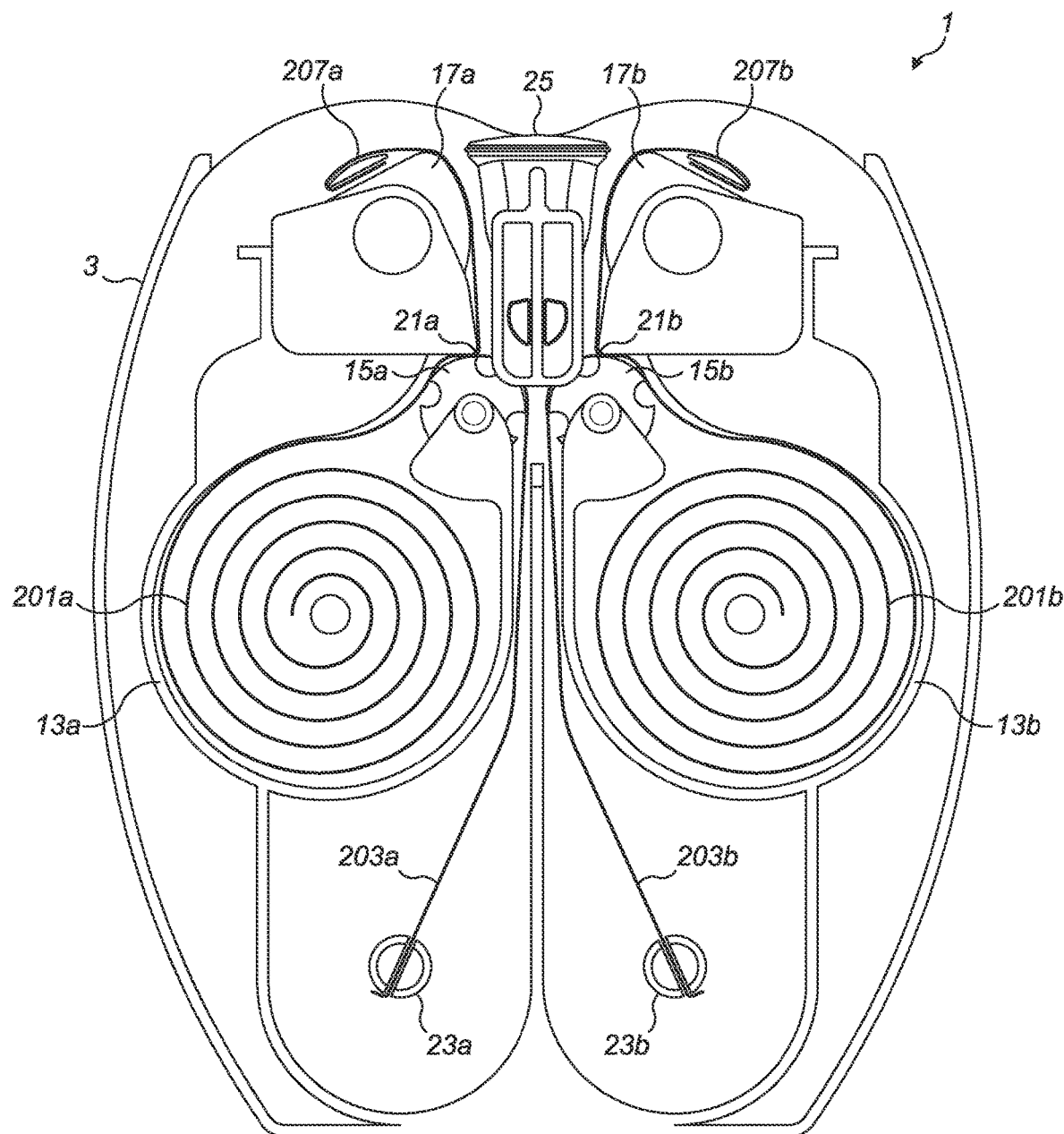
FIG. 3 is a view of the inhaler shown in FIG. 1 with certain components removed and including a pair of the medicament carriers shown in FIG. 2 installed.
Figure 4:
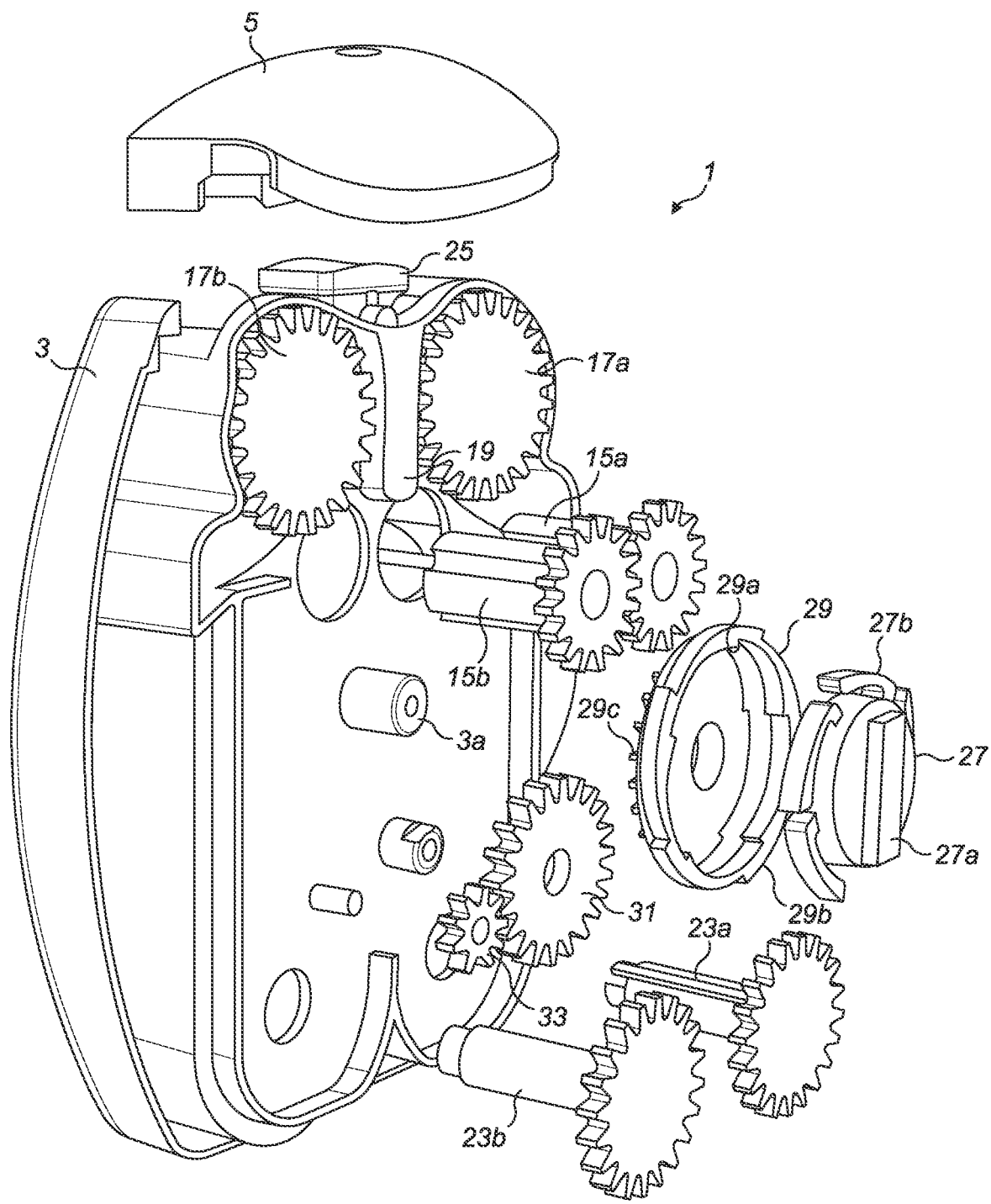
FIG. 4 is an exploded perspective view of the inhaler shown in FIG. 1 with certain components removed, from the opposite direction.

FIGS. 1, 3 and 4 show a dry powder inhaler 1 according to a non-limiting embodiment of the invention. FIG. 2 shows a medicament carrier 201 for use with the inhaler 1. A dry powder inhaler using the same type of medicament carrier and having a manifold component is described in WO 2007/068896 A1, the entire contents of which is incorporated herein by reference.

As shown in FIG. 1, the inhaler 1 is a hand-held device having a substantially flat or planar shape with a rounded outer profile. The outer profile of the inhaler is mainly defined by its housing 3 which encloses its internal components and receives at least one medicament carrier 201 (not shown in FIG. 1 but shown in FIGS. 2 and 3). Extending from the housing 3 is a mouthpiece component 5 having a central opening through which the user inhales the powder medicament. The mouthpiece component 5 is assembled or joined to the housing 3.

The inhaler also comprises a mouthpiece cover 7, which is rotatably connected to the housing 3 for sequential movement about a rotation axis from a first position in which the mouthpiece 5 is completely covered to a second position in which the mouthpiece 5 is also completely covered, and from the second position to a third position in which the mouthpiece 5 is completely uncovered. FIG. 1 shows the mouthpiece cover 7 in its third position.

Also visible in FIG. 1 is an air inlet 9 and a dose counter display 11. The air inlet 9, which can be covered by the mouthpiece cover 7, defines the start of an air flow path that extends from the air inlet 9 to the central opening of the mouthpiece 5. The dose counter display 11 is coupled to a dispensing mechanism of the inhaler 1, to be described subsequently, so as to provide an indication of the number of medicament doses used or remaining in the inhaler 1.

FIG. 2 shows a medicament carrier 201 for use with the inhaler 1 shown in FIG. 1. The medicament carrier 201 is in the form of an elongate blister strip. The blister strip comprises a semi-rigid base layer 203 which is formed with spaced-apart blister openings 205 and more flexible cover layer 207 which covers the blister openings 205 to define spaced-apart blisters 209. The blisters 209 each contain a sealed dose of powder medicament.

The cover layer 207 of the medicament carrier 201 is adhesively bonded to the base layer 203 such that the layers 203, 207 can be peeled apart to open the blisters 209 and liberate the powder medicament without any risk of either layer 203, 207 breaking. The base layer 203 and the cover layer 207 typically comprise plastics/aluminium laminates and are adhesively bonded by a heat seal lacquer. A suitable medicament carrier is described in more detail in WO 2007/068896 A1.

The inhaler 1 shown in FIG. 1 is designed for use with a pair (i.e. two) of the medicament carriers 201 shown in FIG. 2, as will now be described with reference to FIG. 3. It is to be noted, however, that embodiments according to the invention may be used with, or comprise, any number of the medicament carriers 201, including just one.

FIG. 3 is a view of the inhaler 1 shown in FIG. 1 with certain components removed and including a pair of the medicament carriers 201a, 201b installed. In particular, the mouthpiece 5, mouthpiece cover 7, and part of the housing 3 have been removed to reveal a remaining part of the housing 3 and the medicament carriers 201a, 201b (shown in schematic form, without all of the blisters), as well as a manifold component 25, to be described subsequently, and parts of the dispensing mechanism. As shown in the drawing, the housing 3 provides regions 13a, 13b for accommodating unused portions of the medicament carriers 201a, 201b, which are loosely-coiled. Regions are also provided for accommodating used portions of the medicament carriers 201a, 201b, as will be described below. It is noted that the internal arrangement of the inhaler 1 is generally symmetrical, with one medicament carrier 201a being accommodated on one side (left side in the drawing) and the other medicament carrier 201b being accommodated on the other side (right side in the drawing).

The dispensing mechanism, which is only partly shown in FIG. 3, comprises an indexing wheel 15a, 15b and a peeling spool 17a, 17b for each of the medicament carriers 201a, 201b. Each medicament carrier 201a, 201b is fed around its respective indexing wheel 15a, 15b with the base layer 203a, 203b having the blisters facing the indexing wheel 15a, 15b. The indexing wheels 15a, 15b are provided with a plurality of recesses about their circumference which are sized and positioned to receive the blisters of the medicament carrier 201a, 201b. When the index wheels 15a, 15b are rotatably driven by the dispensing mechanism, they engage the medicament carriers 201a, 201b, in particular their semi-rigid blisters, so that the next medicament-containing blister of each medicament carrier 201a, 201b can be advanced to a dispensing position of the inhaler 1 (adjacent the manifold component 25, at which the medicament is to be presented for inhalation).

Simultaneously, a leading end of the cover layer 207a, 207b of each medicament carrier 201a, 201b is separated from its base layer 203a, 203b and fed around a peeling edge 21a, 21b, which is positioned between used portions of the cover layer 207a, 207b and the base layer 203a, 203b. For this purpose, the leading end of the cover layer 207a, 207b of each medicament carrier 201a, 201b is attached to a respective peeling spool 17a, 17b. The peeling spools 17a, 17b are rotatably driven at the same time as the indexing wheels 15a, 15b, and this causes each cover layer 207a, 207b to be gradually peeled away from its base layer 203a, 203b at the peeling edge 21a, 21b, so that the medicament-containing blister 209a, 209b is opened for inhalation by the user.

As medicament doses are dispensed from the inhaler 1, used portions of the cover layers 207a, 207b are wound onto the peeling spools 17a, 17b. Used portions of the base layers 203a, 203b are accommodated in a separate region of the housing where they are coiled up by rotatably-driven coiling spools 23a, 23b. By way of example, the medicament carriers 201a, 201b may each comprise 60 doses of a powder medicament, with a dose from each carrier being dispensed simultaneously.

The manifold component 25 and the remaining parts of the dispensing mechanism of the inhaler 1 will now be described with reference to FIG. 3 and FIG. 4, which is an exploded perspective view of the inhaler shown in FIG. 1 with certain components removed. It is noted that FIG. 4 shows an opposite side of the inhaler to that shown in FIG. 3, i.e. FIG. 4 shows the back side of the inhaler 1. In FIG. 4, the mouthpiece cover 7, and part of the housing 3 have been removed to reveal a remaining part of the housing 3 and remaining parts of the dispensing mechanism. FIG. 4 also shows the mouthpiece 5 and part of the manifold component 25.

The manifold component 25 shown in FIGS. 3 and 4 is a unitary moulded plastics component arranged in the housing 3 and which defines an air flow path extending from the air inlet 9 (FIG. 1) to the mouthpiece 5, with which it interfaces. When a user inhales through the mouthpiece 5, air is drawn in to the air inlet 9, through the air flow path, and out through the mouthpiece 5. The manifold component 25 is arranged in such a way that the air flow path is provided with multiple openings adjacent to the dispensing position 19 of the inhaler, so that the medicament doses of opened blisters are placed in fluid communication with the air flow path. In this way, when the user inhales through the mouthpiece 5, the powder medicament can be drawn out of the blisters by the turbulent air flow and inhaled.

FIG. 4 shows the back sides of the indexing wheels 15a, 15b, peeling spools 17a, 17b and coiling spools 23a, 23b, each of which is rotatably mounted in the housing and provided with a gear wheel for driven rotation. The gear wheels form part of a gear train which is driven by opening the mouthpiece cover 7 (FIG. 1).

For this purpose, the mouthpiece cover 7 (not shown in FIG. 4) is coupled to a first gear wheel 27, which is arranged to rotate with the mouthpiece cover 7 about its rotation axis. In particular, the first gear wheel 27 is arranged to rotate forwards and backwards when the mouthpiece cover 7 is opened and closed.

The first gear wheel 27 is arranged to selectively drive a second gear wheel 29 which is mounted coaxially with the first gear wheel 27 on a stub shaft 3a. The second gear wheel 29 is a drive gear of the dispensing mechanism and directly or indirectly drives the indexing wheels 15a, 15b, peeling spools 17a, 17b and coiling spools 23a, 23b when the mouthpiece cover 7 is opened. The coiling spools 23a, 23b are also driven via idler gear wheels 31, 33. The first and second gearwheels 27, 29 will now be described in greater detail.

The first gear wheel 27 is directly coupled to a hub of the mouthpiece cover 7, which is covered by the housing 3 in FIG. 1. For this purpose, a front face of the first gear wheel 27 is provided with a raised rib 27a, which is received into a corresponding slot of the hub. When the mouthpiece cover 7 is opened and closed, the slot engages the rib 27a to transmit torque, so that the first gear wheel 27 rotates with the mouthpiece cover 7.

The outer circumference of the first gear wheel 27 is provided with a plurality, in this embodiment five, resilient drive pawls 27b which are equally spaced-apart at an angle of 72 degrees. It should be noted that other embodiments may comprise a different number of resilient drive pawls 27b. For example, another preferred embodiment comprises four resilient drive pawls which are equally spaced-apart at an angle of 90 degrees.

The resilient drive pawls 27b of the first gear wheel 27 are arranged to selectively engage corresponding ratchet teeth 29a formed as an internal gear on the second gear wheel 29. In particular, when the first gear 27 is rotated forwards upon opening of the mouthpiece cover 7, the resilient drive pawls 27b come into contact with and engage the ratchet teeth 29a of the second gear wheel 29 so as to drive it forwards. However, when the first gear 27 is rotated backwards upon closing of the mouthpiece cover 7, the resilient drive pawls 27b slide over the ratchet teeth 29a of the second gear wheel 29 so that it is not driven.

The second gear wheel 29 is provided about its outer circumference with a second plurality of ratchet teeth 29b which function, together with a fixed pawl attached to the housing (not shown), as a means for preventing reverse rotation of the second gear wheel 29.

The second gear wheel 29 is also provided about its outer circumference, in a different axial plane, with a set of ordinary gear teeth 29c which engage and drive a first one of the indexing wheels 15b. This indexing wheel 15b drives the other indexing wheel 15a and a first one of the peeling spools 17b. The other indexing wheel 15a drives the other peeling spool 17a. It will be understood that the gear train is sequenced so as to ensure that each of the driven elements rotates in the appropriate direction for dispensing the powder medicament from the blisters of the medicament carriers 201a, 201b.

Further detail relating to the structure and design of a suitable dispensing mechanism can be found for example in WO 2007/068896 A1.

Figure 5A:
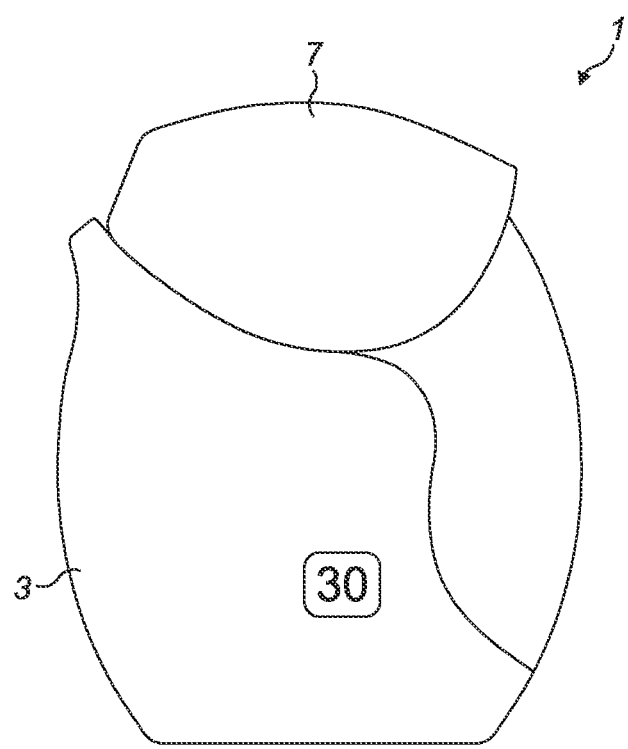
FIGS. 5a and 5b are schematic views showing the inhaler and a part of its dispensing mechanism in a first position of the mouthpiece cover.
Figure 5B:
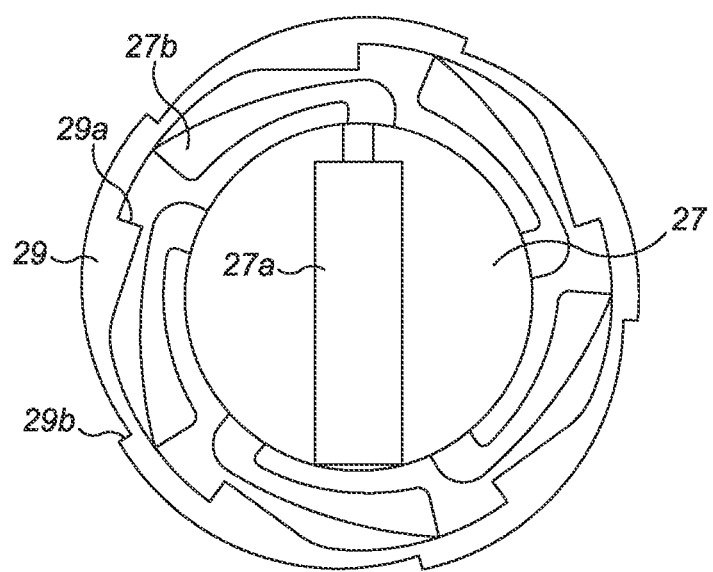
Figure 6A:
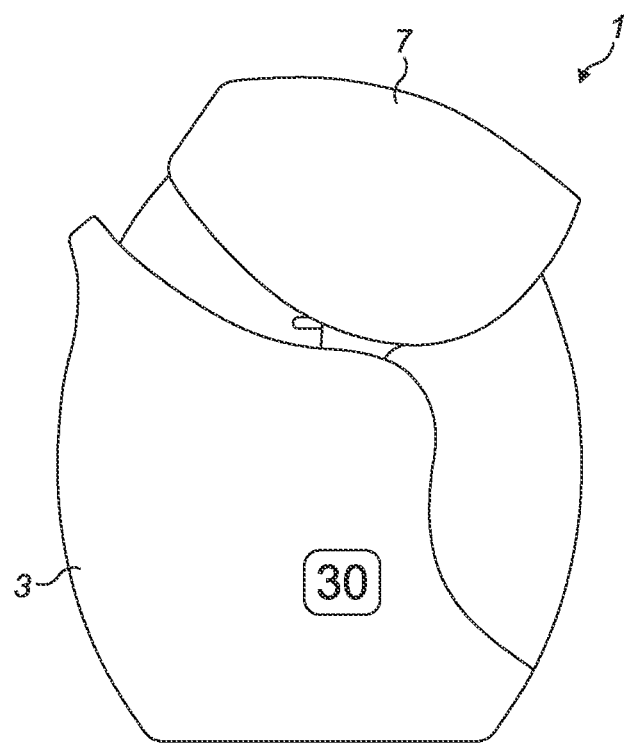
FIGS. 6a and 6b are schematic views showing the inhaler and a part of its dispensing mechanism in a second position of the mouthpiece cover.
Figure 6B:
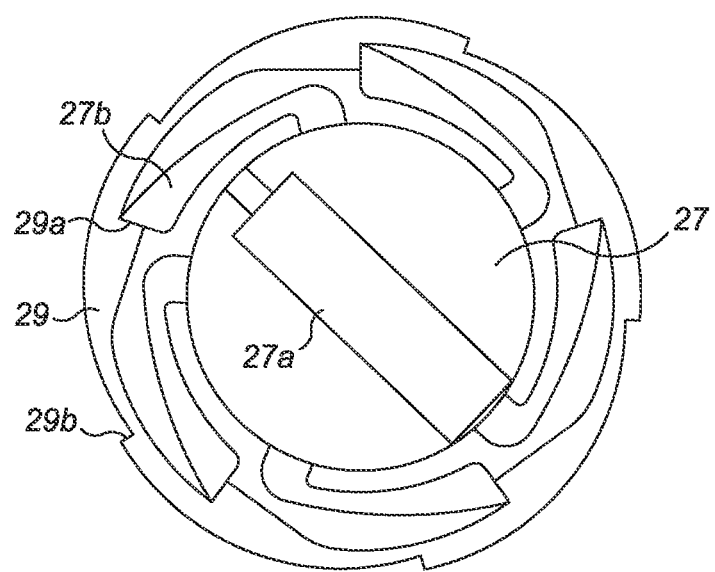
Figure 7A:
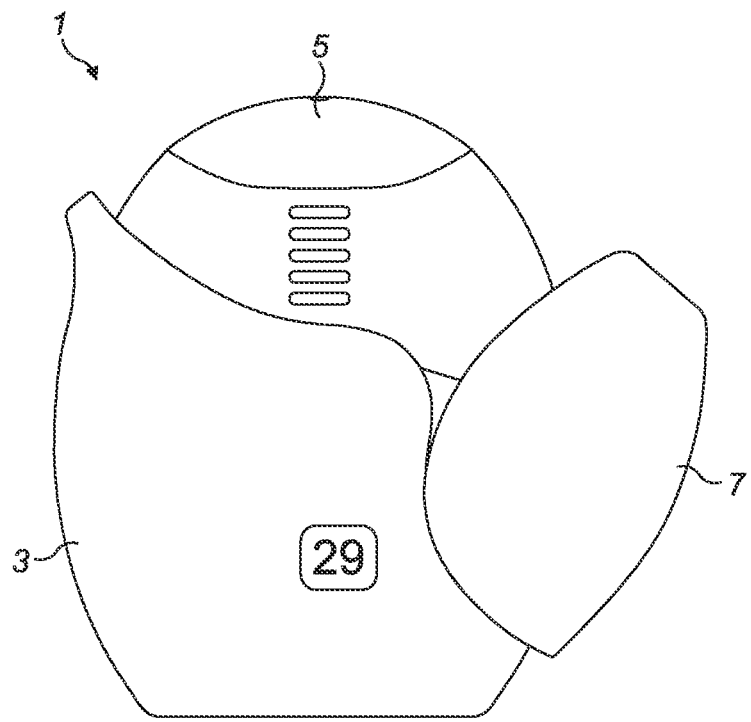
FIGS. 7a and 7b are schematic views showing the inhaler and a part of its dispensing mechanism in a third position of the mouthpiece cover.
Figure 7B:
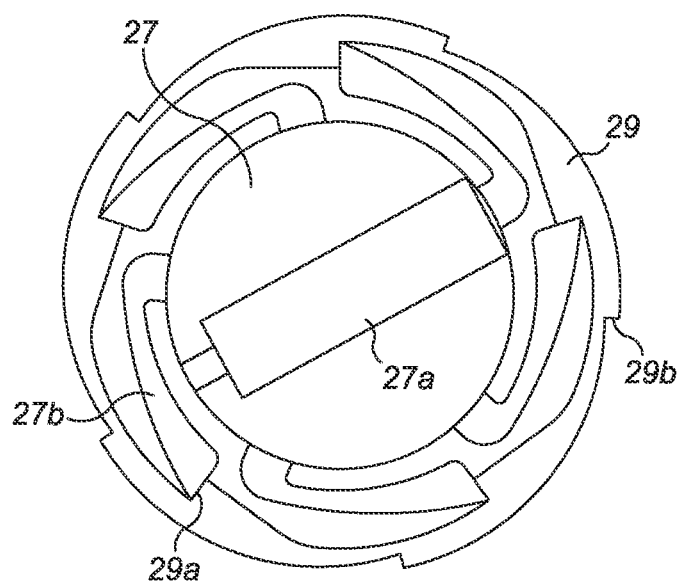

Operation of the dispensing mechanism, will now be described with reference to FIGS. 5a to 7b. FIGS. 5a and 5b are schematic views showing the inhaler 1 and a part of its dispensing mechanism in a first position of the mouthpiece cover 7. FIGS. 6a and 6b are schematic views showing the inhaler 1 and a part of its dispensing mechanism in a second position of the mouthpiece cover 7. FIGS. 7a and 7b are schematic views showing the inhaler 1 and a part of its dispensing mechanism in a third position of the mouthpiece cover 7. It is noted that FIGS. 5b, 6b and 7b show an opposite (back) side of the inhaler to that shown in FIGS. 5a, 6a and 7a (which is a front side).

Referring now to FIG. 5a, the inhaler 1 is shown with the mouthpiece cover 7 in its first position, which is its normal (completely closed) position when the inhaler 1 is not in use. In this position, the mouthpiece 5 is completely covered by the mouthpiece cover 7 and the mouthpiece cover 7 is rotated to the maximum extent possible in the counter-clockwise direction (also referred to herein as the backwards direction). In this position, the mouthpiece 5 is completely protected from contamination. Such contamination can be unhygienic and can potentially affect the medicament delivery performance of the inhaler 1.

FIG. 5b is a view showing the first gear wheel 27 and second gear wheel 29 when the mouthpiece cover 7 is in the first position shown in FIG. 5a. In this position, the resilient drive pawls 27b of the first gear wheel 27 are spaced away from, and are not therefore engaged with, the corresponding ratchet teeth 29a formed as an internal gear on the second gear wheel 29.

FIG. 6a shows the inhaler 1 after the mouthpiece cover 7 has been moved from the first position to the second position. In this position, the mouthpiece cover 7 has rotated clockwise (or forwards) but the mouthpiece 5 is still completely covered by the mouthpiece cover 7. Movement of the mouthpiece cover 7 from the first position to the second position may enclose an angle of at least 5 degrees and, in the illustrated embodiment, encloses an angle of 10 degrees.

FIG. 6b is a view showing the first gear wheel 27 and second gear wheel 29 when the mouthpiece cover 7 is in the second position shown in FIG. 6a. In this position, the first gear wheel 27 has rotated forwards (counter-clockwise in this view) to bring the resilient drive pawls 27b just into contact with the corresponding ratchet teeth 29a of the second gear wheel 29. The second gear wheel 29 has not, however, moved, and so the dispensing mechanism of the inhaler 1 has not yet been driven.

FIG. 7a shows the inhaler 1 after the mouthpiece cover 7 has been moved from the second position to the third position. In this position, the mouthpiece cover 7 has rotated further clockwise (or forwards) to completely uncover the mouthpiece 5 ready for the user to inhale dispensed doses of the powder medicament. In this position, the mouthpiece cover 7 is rotated to the maximum extent possible in the clockwise direction. For reasons that will become apparent from the following description, movement of the mouthpiece cover 7 from the second position to the third position encloses an angle of exactly 72 degrees. This implies that, in the illustrated embodiment, movement of the mouthpiece cover 7 from the first position to the third position encloses a total angle of 82 degrees (i.e. 10 degrees plus 72 degrees).

FIG. 7b is a view showing the first gear wheel 27 and second gear wheel 29 when the mouthpiece cover 7 is in the third position shown in FIG. 7a. In this position, the first gear wheel 27 has rotated further forwards (counter-clockwise in this view) and in this case the resilient drive pawls 27b have engaged the corresponding ratchet teeth 29a of the second gear wheel 29 to drive the second gear wheel 29 forwards. This driving of the second gear wheel 29 functions to drive the dispensing mechanism so that the next medicament-containing blister of each medicament carrier 201a, 201b is moved to the dispensing position 19 of the inhaler 1 and so that the cover layers 207a, 207b are peeled away to place the medicament doses in fluid communication with the air flow passage of the manifold 25, ready for inhalation by the user.

The mouthpiece cover 7 is configured so that movement from the second position to the third position encloses an angle of exactly 72 degrees because this results in the five resilient drive pawls 27b of the first gear wheel 27 and the corresponding five ratchet teeth 29a of the second gear wheel 29 rotating through 72 degrees so that they start and end with the same angular positions, as can be seen by comparing FIGS. 6b and 7b, which facilitates resetting the device when the mouthpiece cover 7 is subsequently closed.

In particular, when the mouthpiece cover 7 is closed after use of the inhaler 1, by rotating the mouthpiece cover 7 counter-clockwise from the third position shown in FIG. 7a to the first position shown in FIG. 5a, the second gear wheel 29 is prevented from rotating backwards (clockwise in the views of FIGS. 5b, 6b and 7b) owing to the means for preventing reverse rotation 29b and therefore remains in the same angular position. The first gear wheel 27 rotates backwards (clockwise in the views of FIGS. 5b, 6b and 7b) as the mouthpiece cover 7 is closed, with the resilient drive pawls 27b sliding back over the ratchet teeth 29a of the second gear wheel 29 to the position shown in FIG. 6b and then back to the position shown in FIG. 5b.

With the mouthpiece cover 7 closed, the five resilient drive pawls 27a of the first gear wheel 27 and the corresponding five ratchet teeth 29a of the second gear wheel 29 have the positions shown in FIG. 5b, ready for the next use.

The inhaler 1 described above comprises a first gearwheel 27 having five resilient drive pawls 27b. It should be noted that the first gearwheel may instead comprise a different number of resilient drive pawls. For example, the first gear wheel may be provided with four resilient drive pawls equally spaced-apart at 90 degree intervals (and correspondingly the second gear wheel may be provided with four ratchet teeth equally spaced-apart at 90 degree intervals), in which case movement of the mouthpiece cover from the second position to the third position would encloses an angle of exactly 90 degrees (360 degrees divided by four).

The inhaler 1 described above provides an arrangement in which movement of the mouthpiece cover 7 from the first position shown in FIG. 5a to the second position shown in FIG. 6a does not result in any actuation of the dispensing mechanism and does not uncover the mouthpiece 5, even partly. As such, actuation caused by unintentional or accidental movement of the mouthpiece cover when the inhaler is not in use can be avoided. Further, such unintentional or accidental movement of the mouthpiece cover does not risk of contamination of the mouthpiece, since the mouthpiece remains completely covered.

The manifold component 25 of the inhaler 1 will now be described in detail. As noted above, the manifold component 25 may be a unitary moulded plastics component arranged in the housing 3 and which defines an air flow path extending from the air inlet 9 (FIG. 1) to the mouthpiece 5, with which it interfaces.

The manifold component 25 may be formed of any polymer-based material that is suitable for moulding. Such materials include: polyolefins, including polyethylene, in particular high density polyethylene (HDPE), and polypropylene; polyesters, including polyethylene terephthalate; polyamides, including nylons; thermosetting polymers, including urea-formaldehyde, melamine, epoxy resins and polyimides; and mixtures or copolymers thereof.

Figure 8:
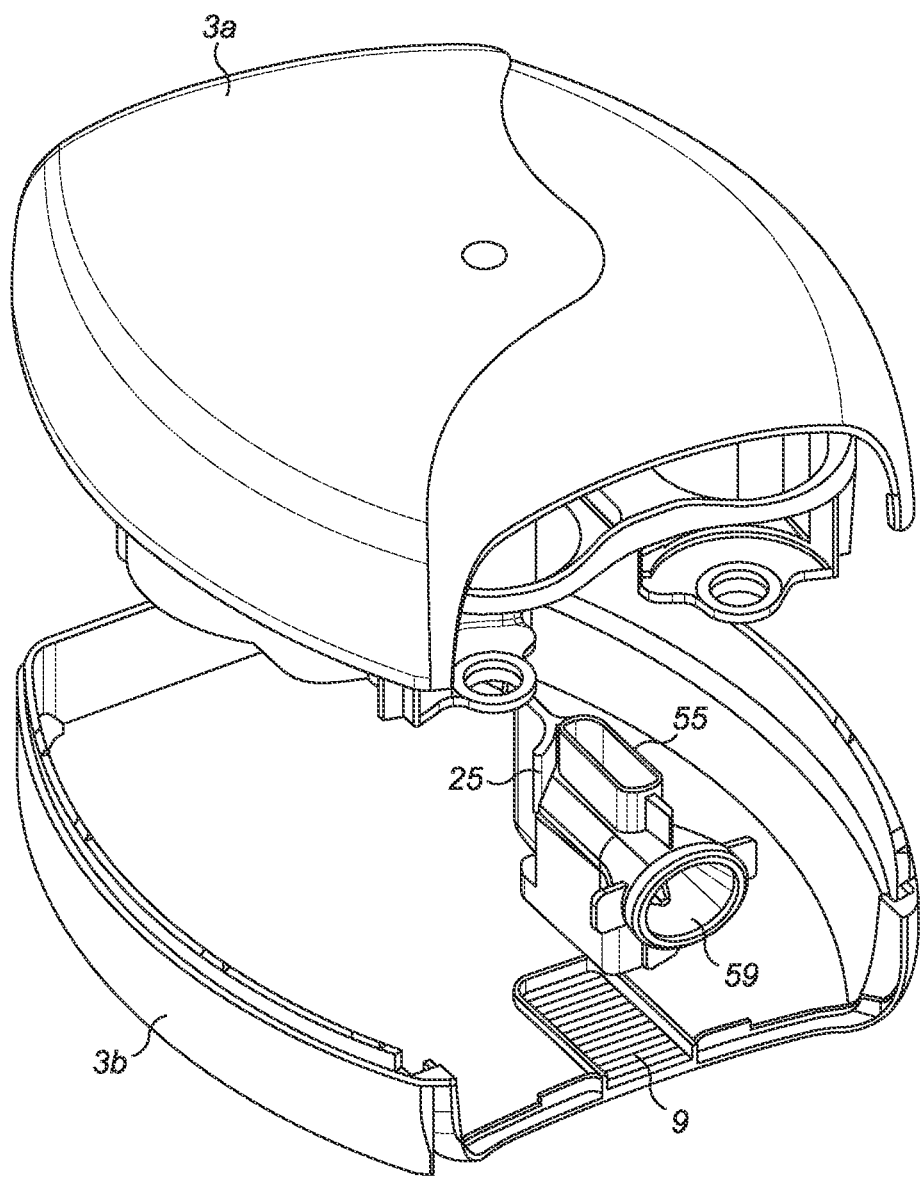
FIG. 8 is an exploded perspective view showing a manifold component of the inhaler together with components forming a housing of the inhaler.

FIG. 8 is an exploded perspective view showing the manifold component 25 of the inhaler 1 together with a pair of shell-like components 3a, 3b that form the housing 3. The remaining components of the inhaler 1 have been omitted from FIG. 8 for clarity reasons. The manifold component 25 is arranged in the housing, in the illustrated orientation, so as to interface with the air inlet 9 and the mouthpiece 5 (not shown in FIG. 8), between which it provides the air flow path. The manifold component 25 also interfaces with the opened blisters of the blister packs (not shown in FIG. 8).

Figure 9:
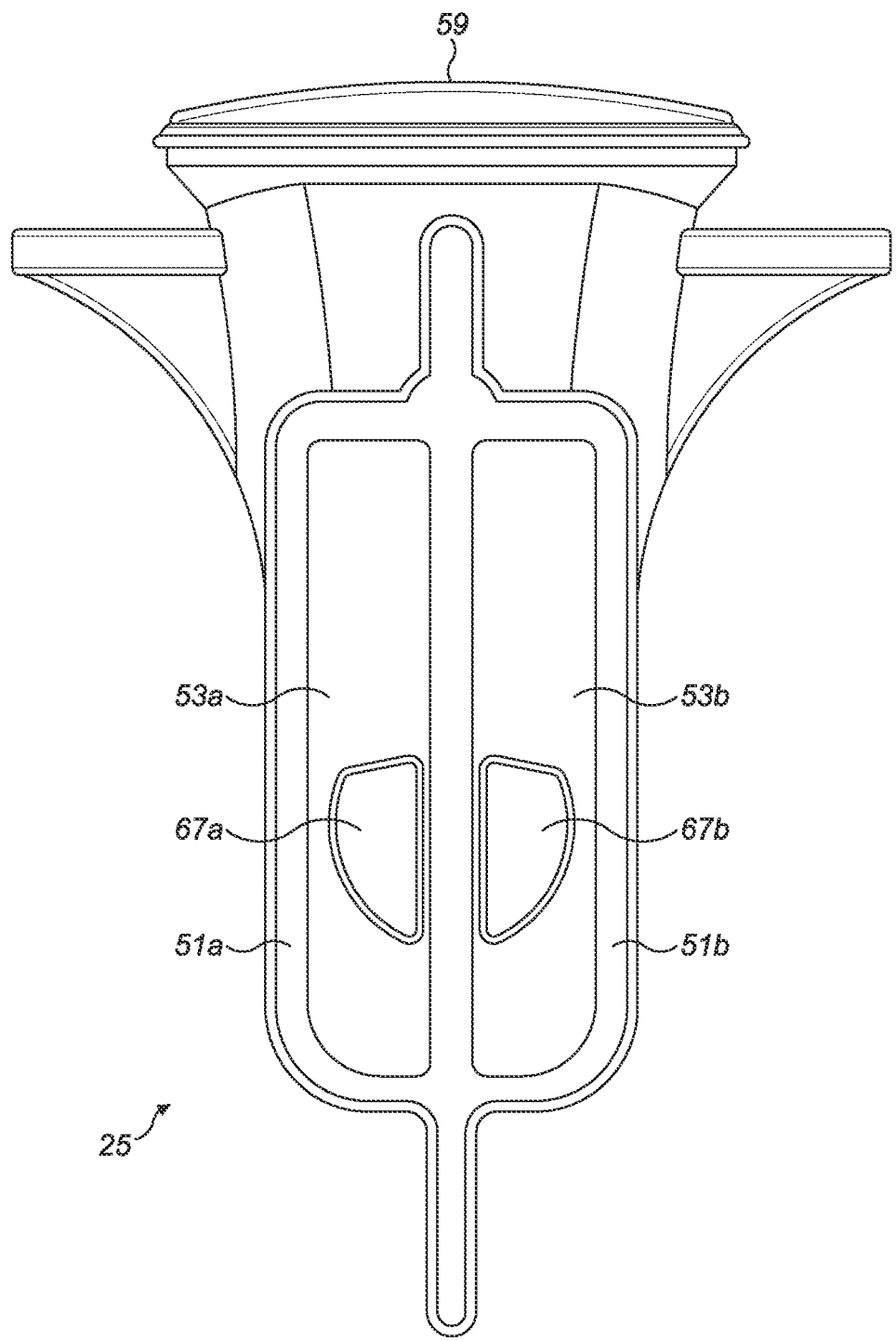
FIG. 9 is a top view of the manifold component.
Figure 10:
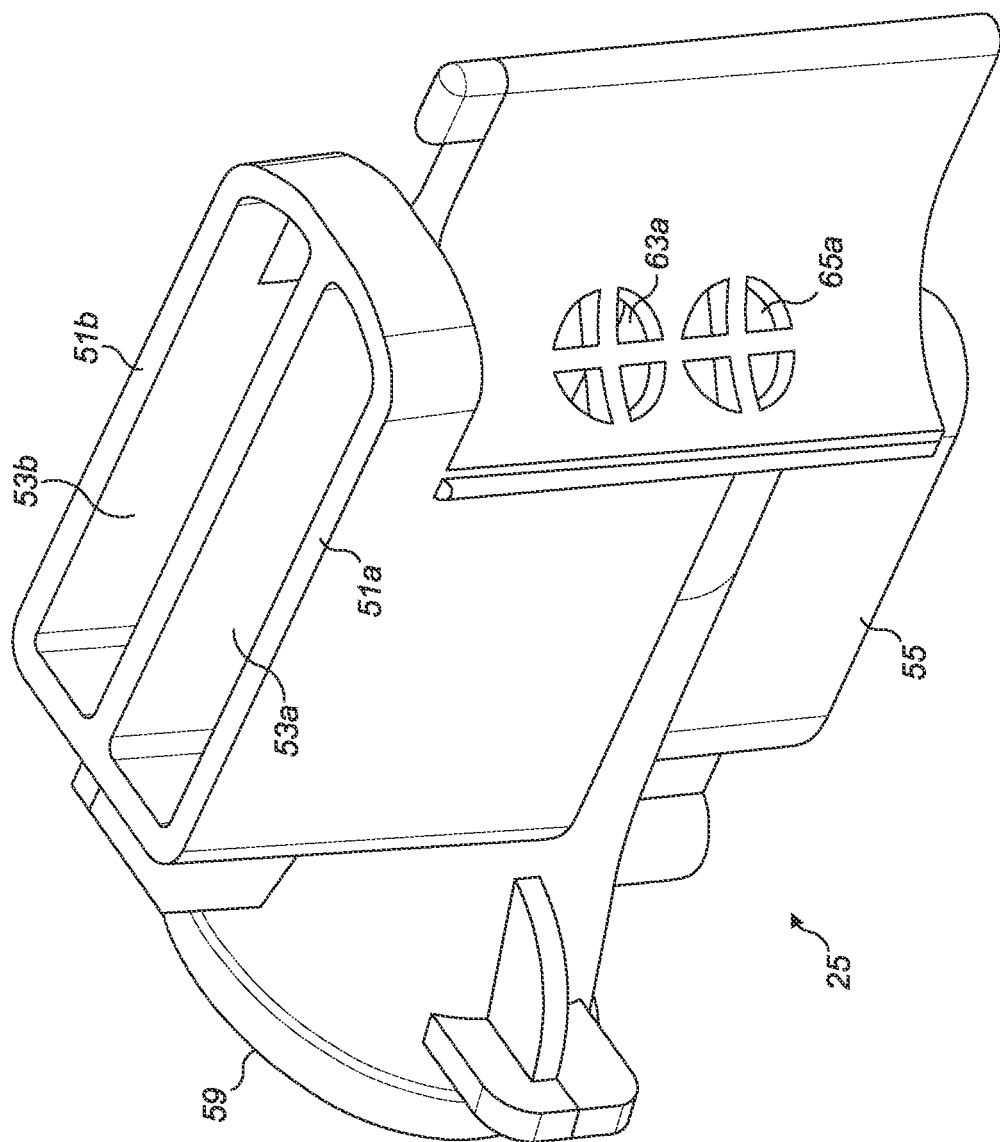
FIG. 10 is a perspective view of the manifold component.
Figure 11:
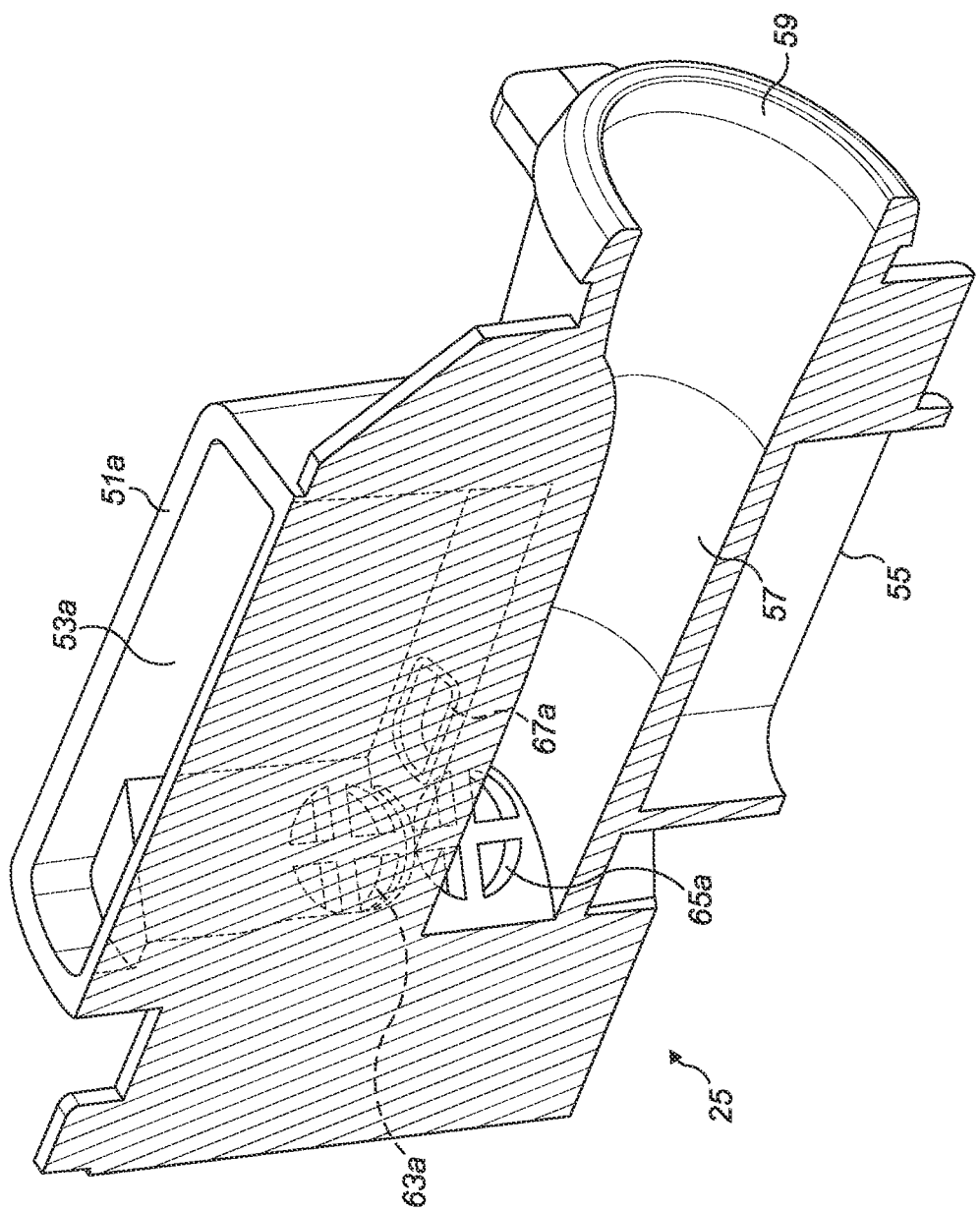
FIG. 11 is a sectioned perspective view of the manifold component.
Figure 12:
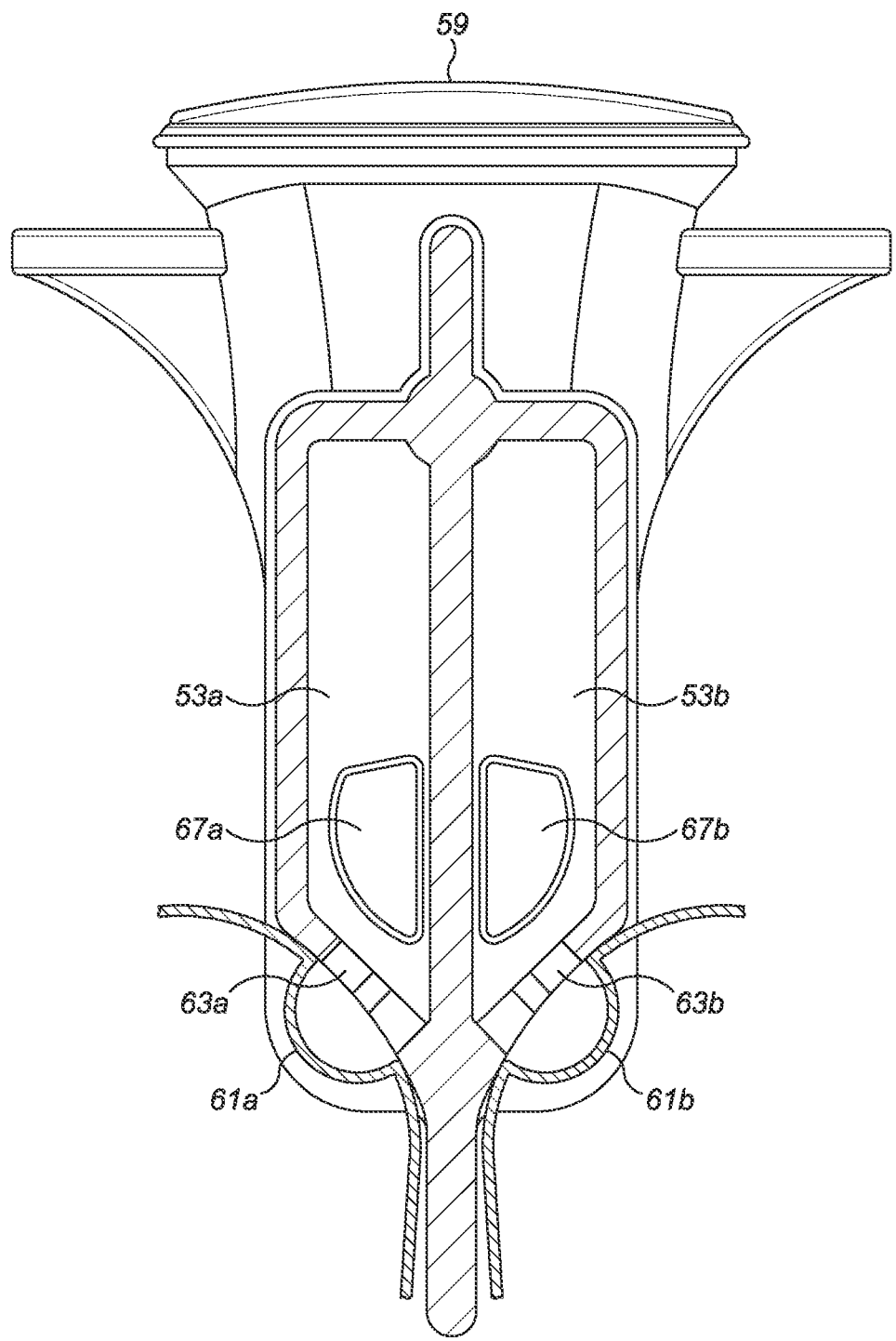
FIG. 12 is a sectioned top view of the manifold component interfacing with a pair of adjacent blister packs.

FIGS. 9 to 12 illustrate the manifold component 25 in greater detail. FIG. 9 is a top view of the manifold component 25 and FIG. 10 is a perspective view of the manifold component 25. FIGS. 11 and 12 are sectioned views of the manifold component 25; the former being a perspective view (taken from the opposite side to that of FIG. 10; also showing hidden detail) and the latter being a top view. The manifold component 25 has a number of moulded structures which are described below. FIG. 12 also illustrates first and second opened blisters 61*a*, 61*b* of the respective blister packs, with which the manifold component 25 interfaces, in use.

More specifically, the manifold component 25 comprises first and second air inlet openings 51*a*, 51*b* for receiving external air directly from the air inlet 9. A first air conduits 53*a* extends from the first air inlet opening 51*a* and a second air conduits 53*b* extends from the second air inlet opening 51*b*. Both the air inlet openings 51*a*, 51*b* and the air conduits 53*a*, 53*b* have an elongate cross section and are arranged side-by-side, separated by a narrow wall.

The air conduits 53*a*, 53*b* are separately formed so that the external air from each of the first and second air inlet openings 51*a*, 51*b* does not mix with the external air from the other of the first and second air inlet openings 51*a*, 51*b* before reaching the first and second opened blister pockets 61*a*, 61*b*, as will be explained below. Furthermore, the first and second air inlet openings 51*a*, 51*b* preferably define the only points of entry for external air into the manifold component 25 (and into the inhaler 1).

An end of the manifold component 25 opposing the air inlet openings 51*a*, 51*b* is provided with a mounting protrusion 55 (FIG. 8) which is engaged in a corresponding recess of the housing 3. It should be noted that the mounting protrusion 55 does not define any part of the air flow path and is provided only for assembly purposes.

The manifold component 25 also comprises a medicament delivery conduit 57 which opens out into a medicament outlet opening 59 for delivery of air-entrained medicament from first and second opened blister pockets to the mouthpiece 5 (not shown in FIGS. 8 to 12), and on to the user. The medicament delivery conduit 57 and the medicament outlet opening 59 both have a generally circular cross section. The medicament delivery conduit 57 partly tapers along its length, with an increasing cross sectional area in the direction of air flow.

As illustrated most clearly in FIG. 11, the first and second air conduits 53*a*, 53*b* are arranged in the manifold component 25 to be adjacent to the medicament delivery conduit 57 (although only the first air conduit 53*a* is visible in FIG. 11). The air conduits 53*a*, 53*b* are separated from the manifold component 25 by narrow walls.

Furthermore, it can be seen from FIG. 11 that the first and second air conduits 53*a*, 53*b* extend in a direction (vertically in the drawing) that is substantially perpendicular to the direction (horizontally in the drawing) in which the medicament delivery conduit 57 extends. In this way, air-entrained medicament can delivered to the mouthpiece 5 in a direction that is substantially perpendicular to the direction in which external air is received from the air inlet 9, so as to accommodate the relative orientations of the mouthpiece 5 and air inlet 9 of the inhaler 1. This arrangement also allows the air-entrained medicament to pass from the opened blister pockets to the mouthpiece 5 without traversing any bends, which could lead to undesirable medicament deposition and build up on the surfaces of the medicament delivery conduit 57.

The manifold component 25 also comprises a first air outlet opening 63*a* for providing the external air from the first air conduit 53*a* to a first opened blister pocket 61*a*, and a first medicament inlet opening 65*a* for receiving air-entrained medicament from the first opened blister pocket 61*a* and providing it to the medicament delivery conduit 57. As can be seen in FIGS. 10 and 11, the first air outlet opening 63*a* and the first medicament inlet opening 65*a* are arranged side-by-side to enable simultaneous communication with the first opened blister pocket 61*a*. The first air outlet opening 63*a* is provided in a side wall of the first air conduit 53*a*, whereas the first medicament inlet opening 65*a* is provided in an end wall of the medicament delivery conduit 57 (directly facing the medicament outlet opening 59). Correspondingly, the manifold component 25 comprises a second air outlet opening 63*b* (not shown in FIGS. 10 and 11, but having the same size and shape as the first air outlet opening 63*a*) for providing the external air from the second air conduit 53*b* to a second opened blister pocket 61*b*, and a second medicament inlet opening (not shown in FIGS. 10 and 11, but having the same size and shape as the first medicament inlet 65*a*) for receiving air-entrained medicament from the second opened blister pocket 61*b* and providing it to the medicament delivery conduit 57. The second air outlet opening 63*b* and the second medicament inlet opening are mirror images of the first air outlet opening 63*a* and the first medicament inlet opening 65*a*, respectively (see FIG. 12). As such, they are arranged side-by-side to enable simultaneous communication with the second opened blister pocket 61*b*.

Also, the second air outlet opening 63*b* is provided in a side wall of the second air conduit 53*b*, whereas the second medicament inlet opening (not shown) is provided in an end wall of the medicament delivery conduit 57 (directly facing the medicament outlet opening 59).

The air outlet openings and the medicament inlet openings are arranged in curved side walls of the manifold component 25 (referring to FIG. 12). In this way, the blister packs in which the first and second opened blisters 61*a*, 61*b* are provided, are able to slide along the side wall while maintaining substantial contact therewith and providing a substantial fluid (powder and air) seal around the opened blister pockets 61*a*, 61*b*.

As has been noted above, the first and second air conduits 53*a*, 53*b* are separately formed in the manifold component 25 so that the external air from each of the first and second air inlet openings 51*a*, 51*b* does not mix with the external air from the other of the first and second air inlet openings 51*a*, 51*b* before reaching the first and second opened blister pockets 61*a*, 61*b*. By providing separate first and second air conduits 53*a*, 53*b* connecting the air inlet openings 51*a*, 51*b* and the air outlet openings 63*a* of the manifold component, the invention provides at least partly independent air flow paths for the air that passes through the first and second opened blister pockets 61*a*, 61*b*, in particular the part of the air flow paths that are upstream of the opened blister pockets. This allows the air flow paths to be adapted, or "tuned", to suit the different blister pockets, for example different medicament formulations or different dose sizes contained in the blister pockets.

In the illustrated embodiment, the first and second air conduits 53*a*, 53*b* have different air flow resistances. The different air flow resistances may be provided by configuring the first and second air conduits 53*a*, 53*b* to have different cross sections and cross sectional areas. In particular, the first air conduit 53*a* is configured to be slightly narrower than the second air conduit 53*b*, which results in the first air conduit 53*a* having a higher air flow resistance than the second air conduit 53*b*.

In alternative embodiments, the different air flow resistances may be provided by arranging air flow restriction elements inside one or both of the first and second air conduits 53*a*, 53*b*.

In the embodiment shown in the drawings, the manifold component 25 further comprises a first air bypass passage 67*a* which is arranged to provide direct fluid communication between the first air conduit 53*a* and the medicament delivery conduit 57, and a second air bypass passage 67*b* which is arranged to provide direct fluid communication between the second air conduit 53*b* and the medicament delivery conduit 57. The purpose of each air bypass passage 67*a*, 67*b* is to allow a bleed air flow from the respective air conduit 53*a*, 53*b* to the medicament delivery conduit 57, which bleed air flow bypasses the open blister pockets 61*a*, 61*b*. The bleed air flow serves to disruptively impact the air flow in the medicament delivery conduit 57, to thereby create a more turbulent flow, which helps to deagglomerate the powder medicament and prevent its deposition and build up on the surfaces of the medicament delivery conduit 57.

The provision of independent air bypass passages 67*a*, 67*b* provides further scope for the air flow through the first and second air conduits 53*a*, 53*b* to be adapted, or tuned. For example, the length or cross sectional area of the air bypass passages 67*a*, 67*b* may be adapted to independently vary the proportion of the air flow through the air conduits 53*a*, 53*b* that is allowed to pass through the open blister pockets 61*a*, 61*b*. The air bypass passages 67*a*, 67*b* may also be provided with air flow restriction elements, such as baffles or other obstacles.

As has been explained above, the dry powder inhaler 1 comprises two blister packs in the form of first and second blister packs 201*a*, 201*b* (FIG. 3). The dispensing mechanism is arranged to simultaneously open a blister pocket 61*a*, 61*b* of each of the first and second blister packs, and to simultaneously move the first and second blister packs 201*a*, 201*b* so that: the first opened blister pocket 61*a* is aligned with the first air outlet opening 63*a* and the first medicament inlet opening 65*a*; and the second opened blister pocket 61*b* is aligned with the second air outlet opening 63*b* and the second medicament inlet opening. This allows the inhaler to be used for simultaneous inhalation of different medicaments from the opened blister pockets 61*a*, 61*b*.

Additionally or alternatively, the blister pockets 61*a*, 61*b* of the first and second blister packs 201*a*, 201*b* may have a different shape and/or volume. Additionally or alternatively, the pockets 61*a*, 61*b* of the first and second blister packs 201*a*, 201*b* may contain a different mass or volume of the respective medicaments, and/or contain respective medicaments having different particle size distributions.

The blister pockets 61*a*, 61*b* of the first and second blister packs 201*a*, 201*b* may contain different medicaments for simultaneous inhalation where is it preferred that the medicaments do not mix prior to delivery to the user, for example selected from budesonide, formoterol, beclomethasone, fluticasone, salmeterol, albuterol, salbutamol, indacaterol, tiotropium, ipratropium, glycorpyrronium or umeclidinium, vilanterol, or combinations thereof.

The different medicaments for simultaneous inhalation comprise:

LABA or SABA in the first blister pack and an ICS in the second blister pack; or LABA or SABA in the first blister pack and LAMA or SAMA in the second blister pack; or LABA or SABA and LAMA or SAMA in the first blister pack and ICS in the second blister pack, or budesonide in the first blister pack and formoterol in the second blister pack; or beclomethasone in the first blister pack and formoterol in the second blister pack; or fluticasone in the first blister pack and salmeterol in the second blister pack, or fluticasone in the first blister pack and albuterol in the second blister pack, or fluticasone in the first blister pack and vilanterol in the second blister pack, or umeclidinium in the first blister pack and vilanterol in the second blister pack, or two selected from umeclidinium, fluticasone and vilanterol in the first blister pack, the remaining medicament from umeclidinium, fluticasone and vilanterol in the second blister pack.

For example, the different medicaments for simultaneous inhalation comprise:

fluticasone furoate in the first blister pack and vilanterol trifenatate in the second blister pack, or umeclidinium bromide in the first blister pack and vilanterol trifenatate in the second blister pack, or two selected from umeclidinium bromide, fluticasone furoate and vilanterol trifenatate in the first blister pack and the remaining medicament from umeclidinium bromide, fluticasone furoate and vilanterol trifenatate in the second blister pack.

FIG. 12 is a view corresponding to that of FIG. 11 and showing air flow through the manifold component 25, in use of the inhaler 1. In particular, when the user inhales at the mouthpiece 5 (not shown in FIG. 12), external air is drawn into the air conduits 53*a*, 53*b* through the air inlet openings 51*a*, 51*b*.

From each of the air conduits 53*a*, 53*b*, the air flow is drawn into the medicament delivery conduit 57. In particular, a first portion of the air flow is drawn out through the respective air outlet opening 63*a*, 63*b*, through the respective opened blister pocket 61*a*, 61*b*, and back in through the respective medicament inlet opening 65*a* (only one shown in the drawings). This first portion of the air flow entrains the powder medicament contained in the respective opened blister pocket 61*a*, 61*b*. A second portion of the air flow bypasses the opened blister pocket 61*a*, 61*b* and instead travels through the respective air bypass passage 67*a*, 67*b* into the medicament delivery conduit 57.

As illustrated by arrows in FIG. 13, the first and second portions of the air flow collide with each other in the medicament delivery conduit 57, which creates a more turbulent flow, and which helps to deagglomerate the powder medicament and prevent its deposition and build up on the surfaces of the medicament delivery conduit 57.

Non-limiting embodiments of the invention have been described hereinabove with reference to the accompanying drawings. Various changes may be made to these embodiments without departing from the scope of the invention, which is defined by the claims.

For example, the inhalers described hereinabove are for use with blister packs that are peeled open. However, the inhalers may be for use with blister packs that are opened in other ways, for example by piercing or bursting. The blister packs described above are in the form of elongate strips. In other embodiments, the blister packs may be in the form of discs having the blisters arranged about the circumference.

The embodiments described above comprise a specific type of delivery mechanism which is operated by opening a mouthpiece cover. Different types of delivery mechanism may be provided in alterative embodiment, for example, manual lever operated or electrically operated delivery mechanisms.

Although the inhaler described above comprise two medicament carriers, alternative embodiments of the invention may comprise a single medicament carrier, in which case only one half of the dispensing mechanism shown in FIGS. 3 and 4 would be need to be provided.

In this case, a single medicament carrier-containing embodiment of the invention may be configured for simultaneous inhalation of different medicaments by configuring the dispensing mechanism to open two blisters at a time, and providing different blisters of the medicament carrier with different medicaments. For example, the different medicaments for simultaneous inhalation may comprise: budesonide in a first blister and formoterol in a second blister; or beclomethasone in a first blister and formoterol in a second blister; or fluticasone in a first blister and salmeterol in a second blister, or fluticasone in a first blister and albuterol in a second blister, or fluticasone in a first blister and vilanterol in a second blister, or umeclidinium in a first blister and vilanterol in a second blister, or two selected from umeclidinium, fluticasone and vilanterol in a first blister, the remaining medicament from umeclidinium, fluticasone and vilanterol in a second blister. The different medicaments (A and B) could be provided in successive blisters of the blister packs in a repeating arrangement, for example AB AB AB AB . . . or AB BA AB BA AB.

In this case, the manifold component would need to be adapted slightly, with the air outlet openings and the medicament inlet openings being arranged in the same side wall of the manifold component. This would be necessary to facilitate the interface between the manifold component and the first and second opened blister pockets when the first and second opened blister pockets are adjacent blister pockets in the same (single) blister pack.

In the embodiments described above, the manifold component is a unitary (single piece) moulded plastics component. In alternative embodiments, the manifold component may be formed of multiple pieces that are assembled together, and/or may be formed of other materials, and/or may be formed by other processes, for example by machining a solid block of material.

The invention claimed is:

1. A dry powder inhaler for delivering medicament from at least one blister pack, each blister pack having a plurality of spaced-apart blister pockets containing doses of the medicament, the inhaler comprising:
    a housing for accommodating unused and used portions of the at least one blister pack together with a dispensing mechanism for simultaneously opening at least two blister pockets at a time; and
    a manifold component through which air can be drawn in use of the inhaler, wherein the manifold component comprises:
        first and second air inlet openings for receiving external air;
        a first air outlet opening for providing the external air to a first opened blister pocket and a first medicament inlet opening for receiving air-entrained medicament from the first opened blister pocket, the first air outlet opening and the first medicament inlet opening being arranged side-by-side to enable simultaneous communication with the first opened blister pocket;
        a second air outlet opening for providing the external air to a second opened blister pocket and a second medicament inlet opening for receiving air-entrained medicament from the second opened blister pocket, the second air outlet opening and the second medicament inlet opening being arranged side-by-side to enable simultaneous communication with the second opened blister pocket; and
        a medicament outlet opening for delivery of the air-entrained medicament from the first and second opened blister pockets to a user, the first and second medicament inlet openings being fluidly connected to the medicament outlet opening by a medicament delivery conduit formed in the manifold component,
    wherein the first and second air inlet openings are fluidly connected to the first and second air outlet openings by respective first and second air conduits, wherein the air conduits are separately provided so that the external air from each of the first and second air inlet openings does not mix with the external air from the other of the first and second air inlet openings before reaching the first and second opened blister pockets, and
    wherein the first and second air inlet openings define sole points of entry for external air into the manifold component.

2. The dry powder inhaler of claim 1, further comprising a mouthpiece component through which a user is able to inhale the air-entrained medicament from the first and second opened blister pockets, wherein the mouthpiece defines an opening which is fluidly connected to the medicament outlet opening of the manifold component.

3. The dry powder inhaler of claim 1, wherein the first and second air conduits have different lengths and/or different cross sections and/or different cross sectional areas to produce different air flow resistances.

4. The dry powder inhaler of claim 3, wherein the different air flow resistances are provided by arranging air flow restriction elements inside one or both of the first and second air conduits.

5. The dry powder inhaler of claim 1, wherein the manifold component further comprises:
    a first air bypass passage providing direct fluid communication between the first air conduit and the medicament delivery conduit; and
    a second air bypass passage providing direct fluid communication between the second air conduit and the medicament delivery conduit,
    wherein the first and second air bypass passages have different lengths and/or different cross sections and/or different cross sectional areas and/or different positions along the medicament delivery conduit.

6. The dry powder inhaler of claim 5, wherein air flow restriction elements are arranged inside the first and second air bypass passages.

7. The dry powder inhaler of claim 5, wherein the first and second air conduits are arranged to be adjacent to the medicament delivery conduit and separated therefrom by walls, wherein the first and second air bypass passages are formed as apertures in the walls.

8. The dry powder inhaler of claim 1, wherein the manifold component is a moulded plastics component.

9. The dry powder inhaler of claim 8, wherein the moulded plastics component is formed of a material selected from the group consisting of:
    polyolefins, including polyethylene, including high density polyethylene (HDPE), and polypropylene;
    polyesters, including polyethylene terephthalate;
    polyamides, including nylons;

thermosetting polymers, including urea-formaldehyde, melamine, epoxy resins and polyimides; and
mixtures or copolymers thereof.

10. The dry powder inhaler of claim 1, wherein the first and second air conduits are arranged side-by-side and separated by a wall.

11. The dry powder inhaler of claim 1, wherein the medicament delivery conduit has a circular, oval or elliptical cross section.

12. The dry powder inhaler of claim 1, wherein the first and second air conduits extend in a direction substantially perpendicular to the direction in which the medicament delivery conduit extends.

13. The dry powder inhaler of claim 1, wherein, in use, air is directed from the first and second air outlet openings of the manifold component into the respective first and second opened blisters, and air-entrained medicament is directed from the first and second opened blisters into the respective first and second medicament inlet openings.

14. The dry powder inhaler of claim 1, wherein the dispensing mechanism is configured for simultaneously opening at least three blister pockets at a time, and wherein the manifold component further comprises:
a third air inlet opening for receiving external air; and
a third air outlet opening for providing the external air to a third opened blister pocket and a third medicament inlet opening for receiving air-entrained medicament from the third opened blister pocket, the third air outlet opening and the third medicament inlet opening being arranged side-by-side to enable simultaneous communication with the third opened blister pocket,
wherein the medicament outlet opening of the manifold component is configured for delivery of the air-entrained medicament from the third opened blister pocket to the user, the third medicament inlet opening being fluidly connected to the medicament outlet opening of the manifold component by the medicament delivery conduit,
and wherein the third air inlet opening is fluidly connected to the third air outlet opening by a third air conduit, wherein the third air conduit is provided separately from the first and second air conduits so that the external air from either of the first and second air inlet openings does not mix with the external air from the third air inlet opening before reaching the third opened blister pocket.

15. The dry powder inhaler of claim 1, further comprising the dispensing mechanism for simultaneously opening at least two blister pockets at a time.

16. The dry powder inhaler according to claim 15, wherein the dispensing mechanism comprises a peeling mechanism arranged to open the blister pockets by peeling a cover layer of the at least one blister pack from a base layer of the at least one blister pack.

17. The dry powder inhaler according to claim 15, wherein the dispensing mechanism comprises an indexing mechanism arranged to move the at least one blister pack so that the first opened blister pocket is aligned with the first air outlet opening and the first medicament inlet opening, and the second opened blister pocket is aligned with the second air outlet opening and the second medicament inlet opening.

18. The dry powder inhaler of claim 1, further comprising the at least one blister pack, wherein each blister pack comprises an elongate base layer defining spaced-apart blister openings containing medicament doses, and a cover layer adhesively bonded to the base layer to close the blister openings, and wherein the cover layer is arranged to be peeled from the base layer.

19. The dry powder inhaler of claim 18, wherein the dry powder inhaler comprises a single blister pack, and wherein the dispensing mechanism is arranged to open at least two blister pockets of the blister pack at a time, these being the first and second opened blister pockets, and to move the blister pack so that the first opened blister pocket is aligned with the first air outlet opening and the first medicament inlet opening, and the second opened blister pocket is aligned with the second air outlet opening and the second medicament inlet opening, such that the dry powder inhaler can be used for simultaneous inhalation of different medicaments from the first and second opened blister pockets.

20. The dry powder inhaler of claim 19, wherein the first and second blister pockets contain different medicaments for simultaneous inhalation, optionally selected from budesonide, formoterol, beclomethasone, fluticasone, salmeterol, albuterol, salbutamol, indacaterol, tiotropium, ipratropium, glycorpyrronium or umeclidinium, vilanterol, or combinations thereof.

21. The dry powder inhaler of claim 20, wherein the different medicaments for simultaneous inhalation comprise:
LABA or SABA in the first blister pocket and an ICS in the second blister pocket; or
LABA or SABA in the first blister pocket and LAMA or SAMA in the second blister pocket; or
LABA or SABA and LAMA or SAMA in the first blister pocket and ICS in the second blister pocket, or
budesonide in the first blister pocket and formoterol in the second blister pocket; or
beclomethasone in the first blister pocket and formoterol in the second blister pocket; or
fluticasone in the first blister pocket and salmeterol in the second blister pocket, or
fluticasone in the first blister pocket and albuterol in the second blister pocket, or
fluticasone in the first blister pocket and vilanterol in the second blister pocket, or
umeclidinium in the first blister pocket and vilanterol in the second blister pocket, or
two selected from umeclidinium, fluticasone and vilanterol in the first blister pocket, the remaining medicament from umeclidinium, fluticasone and vilanterol in the second blister pocket.

22. The dry powder inhaler of claim 20, wherein the different medicaments for simultaneous inhalation comprise:
fluticasone furoate in the first blister pocket and vilanterol trifenatate in the second blister pocket, or
umeclidinium bromide in the first blister pocket and vilanterol trifenatate in the second blister pocket, or
two selected from umeclidinium bromide, fluticasone furoate and vilanterol trifenatate in the first blister pocket and the remaining medicament from umeclidinium bromide, fluticasone furoate and vilanterol trifenatate in the second blister pocket.

23. The dry powder inhaler of claim 20, wherein the first and second blister pockets contain a different mass or volume of the respective medicaments, and/or contain respective medicaments having different particle size distributions.

24. The dry powder inhaler according to claim 18, wherein the dry powder inhaler comprises first and second blister packs, and wherein the dispensing mechanism is arranged to simultaneously open a blister pocket of each of the first and second blister packs, these being the first and second opened blister pockets, and to simultaneously move the first and second blister packs so that the first opened blister pocket is aligned with the first air outlet opening and the first medicament inlet opening, and the second opened blister pocket is aligned with the second air outlet opening and the second medicament inlet opening, such that the dry powder inhaler can be used for simultaneous inhalation of different medicaments from the first and second opened blister pockets.

25. The dry powder inhaler according to claim 24, wherein the blister pockets of the first and second blister packs contain different medicaments for simultaneous inhalation, optionally selected from budesonide, formoterol, beclomethasone, fluticasone, salmeterol, albuterol, salbutamol, indacaterol, tiotropium, ipratropium, glycorpyrronium or umeclidinium, vilanterol, or combinations thereof.

26. The dry powder inhaler of claim 25, wherein the different medicaments for simultaneous inhalation comprise:
LABA or SABA in the first blister pack and an ICS in the second blister pack; or
LABA or SABA in the first blister pack and LAMA or SAMA in the second blister pack; or
LABA or SABA and LAMA or SAMA in the first blister pack and ICS in the second blister pack, or
budesonide in the first blister pack and formoterol in the second blister pack; or
beclomethasone in the first blister pack and formoterol in the second blister pack; or
fluticasone in the first blister pack and salmeterol in the second blister pack, or
fluticasone in the first blister pack and albuterol in the second blister pack, or
fluticasone in the first blister pack and vilanterol in the second blister pack, or
umeclidinium in the first blister pack and vilanterol in the second blister pack, or
two selected from umeclidinium, fluticasone and vilanterol in the first blister pack, the remaining medicament from umeclidinium, fluticasone and vilanterol in the second blister pack.

27. The dry powder inhaler of claim 25, wherein the different medicaments for simultaneous inhalation comprise:
fluticasone furoate in the first blister pack and vilanterol trifenatate in the second blister pack, or
umeclidinium bromide in the first blister pack and vilanterol trifenatate in the second blister pack, or
two selected from umeclidinium bromide, fluticasone furoate and vilanterol trifenatate in the first blister pack and the remaining medicament from umeclidinium bromide, fluticasone furoate and vilanterol trifenatate in the second blister pack.

28. The dry powder inhaler of claim 25, wherein the pockets of the first and second blister packs contain a different mass or volume of the respective medicaments, and/or contain respective medicaments having different particle size distributions.

29. The dry powder inhaler of claim 1, wherein the first and second air outlet openings each defines a central axis which is substantially normal to a plane of the at least one blister pack.

* * * * *